(12) United States Patent
Van Dam et al.

(10) Patent No.: US 9,486,219 B2
(45) Date of Patent: Nov. 8, 2016

(54) BILIARY SHUNTS, DELIVERY SYSTEMS, METHODS OF USING THE SAME AND KITS THEREFOR

(75) Inventors: Jacques Van Dam, San Carlos, CA (US); J. Craig Milroy, Palo Alto, CA (US); R. Matthew Ohline, Redwood City, CA (US)

(73) Assignee: TREUS MEDICAL, INC., Redwood City, CA (US)

(*) Notice: Subject to any disclaimer, the term of this patent is extended or adjusted under 35 U.S.C. 154(b) by 567 days.

(21) Appl. No.: 13/439,251

(22) Filed: Apr. 4, 2012

(65) Prior Publication Data
US 2012/0296257 A1 Nov. 22, 2012

Related U.S. Application Data

(63) Continuation of application No. 12/277,491, filed on Nov. 25, 2008, now abandoned.

(60) Provisional application No. 60/991,682, filed on Nov. 30, 2007, provisional application No. 61/033,368, filed on Mar. 3, 2008.

(51) Int. Cl.
*A61M 5/00* (2006.01)
*A61B 17/11* (2006.01)
(Continued)

(52) U.S. Cl.
CPC ............ *A61B 17/1114* (2013.01); *A61B 17/11* (2013.01); *A61F 2/04* (2013.01); *A61M 27/008* (2013.01); *A61B 2017/00278* (2013.01); *A61B 2017/1139* (2013.01); *A61F 2/064* (2013.01); *A61F 2/24* (2013.01); *A61F 2/2493* (2013.01); *A61F 2002/041* (2013.01);
(Continued)

(58) Field of Classification Search
CPC ............... A61F 2/04; A61F 2002/045; A61F 2002/041; A61B 17/1114
USPC ............... 604/8, 9, 264; 606/153; 623/23.64
See application file for complete search history.

(56) References Cited

U.S. PATENT DOCUMENTS 2,127,903 A 8/1938 Bowen
3,385,300 A 5/1968 Holter
(Continued)

FOREIGN PATENT DOCUMENTS

CN 1220590 A 6/1999
EP 0779062 A1 6/1997
(Continued)

OTHER PUBLICATIONS

Final Office Action received for U.S. Appl. No. 13/410,281 dated May 10, 2013.
(Continued)

*Primary Examiner* — Leslie Deak
(74) *Attorney, Agent, or Firm* — Foley & Lardner LLP

(57) ABSTRACT

The application discloses devices, systems, kits and methods for treating biliary disease. Device comprise, for example, a component configured for deployment between a gallbladder and location within a gastrointestinal tract of a patient which has a proximal end and a distal end with a lumen extending therethrough. A method of deploying the device can be achieved by, for example, creating a duct or fistula between a gallbladder lumen and a portion of a gastrointestinal tract; and providing for drainage from the gallbladder to the gastrointestinal tract.

51 Claims, 34 Drawing Sheets

(51) Int. Cl.

| | | |
|---|---|---|
| *A61F 2/04* | (2013.01) | |
| *A61M 27/00* | (2006.01) | |
| *A61B 17/00* | (2006.01) | |
| *A61F 2/06* | (2013.01) | |
| *A61F 2/24* | (2006.01) | |
| *A61M 25/10* | (2013.01) | |
| *A61M 29/02* | (2006.01) | |
| *A61M 25/02* | (2006.01) | |

(52) U.S. Cl.
CPC ......... *A61M 25/1002* (2013.01); *A61M 29/02* (2013.01); *A61M 2025/0233* (2013.01); *A61M 2025/1072* (2013.01)

(56) References Cited

U.S. PATENT DOCUMENTS

| | | |
|---|---|---|
| 3,818,511 A | 6/1974 | Goldberg et al. |
| 3,834,394 A | 9/1974 | Hunter et al. |
| 3,933,040 A | 1/1976 | Thompson |
| 4,085,757 A | 4/1978 | Pevsner |
| 4,263,917 A | 4/1981 | Moss |
| 4,352,358 A | 10/1982 | Angelchik |
| 4,699,611 A | 10/1987 | Bowden |
| 4,781,677 A | 11/1988 | Wilcox |
| 4,900,303 A | 2/1990 | Lemelson |
| 4,955,859 A | 9/1990 | Zilber |
| 4,968,294 A | 11/1990 | Salama |
| 4,994,066 A | 2/1991 | Voss |
| 5,071,419 A | 12/1991 | Rydell et al. |
| 5,159,925 A | 11/1992 | Neuwirth et al. |
| 5,167,614 A | 12/1992 | Tessmann et al. |
| 5,170,805 A | 12/1992 | Kensey et al. |
| 5,171,311 A | 12/1992 | Rydell et al. |
| 5,197,948 A | 3/1993 | Ghodsian |
| 5,201,746 A | 4/1993 | Shichman |
| 5,259,847 A | 11/1993 | Trambert |
| 5,261,920 A | 11/1993 | Main et al. |
| 5,334,210 A | 8/1994 | Gianturco |
| 5,364,400 A | 11/1994 | Rego et al. |
| 5,443,449 A | 8/1995 | Buelna |
| 5,454,788 A | 10/1995 | Walker et al. |
| 5,466,242 A | 11/1995 | Mori |
| 5,499,994 A | 3/1996 | Tihon et al. |
| 5,514,088 A | 5/1996 | Zakko |
| 5,536,248 A | 7/1996 | Weaver et al. |
| 5,632,762 A | 5/1997 | Myler |
| 5,643,254 A | 7/1997 | Scheldrup |
| 5,709,224 A | 1/1998 | Behl et al. |
| 5,741,333 A | 4/1998 | Frid |
| 5,743,905 A | 4/1998 | Eder |
| 5,755,769 A | 5/1998 | Richard et al. |
| 5,769,880 A | 6/1998 | Truckai et al. |
| 5,776,126 A | 7/1998 | Wilk |
| 5,800,341 A | 9/1998 | McKenna et al. |
| 5,817,046 A | 10/1998 | Glickman |
| 5,824,071 A | 10/1998 | Nelson et al. |
| 5,853,419 A | 12/1998 | Imran |
| 5,860,426 A | 1/1999 | Kleiman |
| 5,876,432 A | 3/1999 | Lau et al. |
| 6,019,757 A | 2/2000 | Scheldrup |
| 6,077,261 A | 6/2000 | Behl et al. |
| 6,077,271 A | 6/2000 | Huebner et al. |
| 6,165,210 A | 12/2000 | Lau et al. |
| 6,241,762 B1 | 6/2001 | Shanley |
| 6,245,101 B1 | 6/2001 | Drasler et al. |
| 6,246,914 B1 | 6/2001 | de la Rama et al. |
| 6,283,992 B1 | 9/2001 | Hankh et al. |
| 6,312,404 B1 | 11/2001 | Agro et al. |
| 6,348,066 B1 | 2/2002 | Pinchuk et al. |
| 6,358,247 B1 | 3/2002 | Altman et al. |
| 6,406,491 B1 | 6/2002 | Vanney |
| 6,409,755 B1 | 6/2002 | Vrba |
| 6,416,545 B1 | 7/2002 | Mikus et al. |
| 6,468,303 B1 | 10/2002 | Amplatz et al. |
| 6,544,291 B2 | 4/2003 | Taylor |
| 6,558,429 B2 | 5/2003 | Taylor |
| 6,585,754 B2 | 7/2003 | Wallace |
| 6,599,299 B2 | 7/2003 | Schultz |
| 6,610,100 B2 | 8/2003 | Phelps et al. |
| 6,616,675 B1 | 9/2003 | Evard |
| 6,641,610 B2 | 11/2003 | Wolf et al. |
| 6,655,386 B1 | 12/2003 | Makower et al. |
| 6,663,663 B2 | 12/2003 | Kim et al. |
| 6,746,489 B2 | 6/2004 | Dua et al. |
| 6,764,519 B2 | 7/2004 | Whitmore |
| 6,945,949 B2 | 9/2005 | Wilk |
| 6,949,080 B2 | 9/2005 | Wolf et al. |
| 6,962,602 B2 | 11/2005 | Vardi et al. |
| 6,964,681 B2 | 11/2005 | Murray |
| 7,004,949 B2 | 2/2006 | Yencho et al. |
| 7,011,095 B2 | 3/2006 | Wolf et al. |
| 7,041,110 B2 | 5/2006 | Yencho et al. |
| 7,094,260 B2 | 8/2006 | Jing et al. |
| 7,118,600 B2 | 10/2006 | Dua et al. |
| 7,144,363 B2 | 12/2006 | Pai et al. |
| 7,182,744 B2 | 2/2007 | Yamasaki et al. |
| 7,294,115 B1 | 11/2007 | Wilk |
| 7,634,319 B2 | 12/2009 | Schneider et al. |
| 7,641,645 B2 | 1/2010 | Schur |
| 7,645,259 B2 | 1/2010 | Goldman |
| 7,647,891 B2 | 1/2010 | Anderson et al. |
| 7,670,364 B2 | 3/2010 | Dusbabek et al. |
| 7,704,223 B2 | 4/2010 | Mantell |
| 7,704,245 B2 | 4/2010 | Dittman et al. |
| 7,717,871 B2 | 5/2010 | Odland |
| 7,717,936 B2 | 5/2010 | Keating et al. |
| 7,722,629 B2 | 5/2010 | Chambers |
| 7,727,225 B2 | 6/2010 | Broaddus et al. |
| 2001/0044647 A1 | 11/2001 | Pinchuk et al. |
| 2002/0032487 A1 | 3/2002 | Dua et al. |
| 2002/0055768 A1 | 5/2002 | Hess et al. |
| 2002/0095110 A1 | 7/2002 | Vanney et al. |
| 2002/0156523 A1 | 10/2002 | Lau et al. |
| 2003/0045828 A1 | 3/2003 | Wilk |
| 2003/0055484 A1 | 3/2003 | Lau et al. |
| 2003/0069533 A1 | 4/2003 | Kakutani et al. |
| 2003/0069606 A1 | 4/2003 | Girouard et al. |
| 2003/0083734 A1 | 5/2003 | Friedrich et al. |
| 2003/0149472 A1 | 8/2003 | Pinchuk et al. |
| 2003/0163079 A1 | 8/2003 | Burnett |
| 2003/0216733 A1 | 11/2003 | McClurken et al. |
| 2004/0073317 A1 | 4/2004 | Schultz |
| 2004/0093058 A1 | 5/2004 | Cottone et al. |
| 2004/0102855 A1 | 5/2004 | Shank |
| 2004/0181150 A1 | 9/2004 | Evans et al. |
| 2004/0199262 A1 | 10/2004 | Dua et al. |
| 2004/0211434 A1* | 10/2004 | Loomas et al. ............... 128/898 |
| 2004/0215331 A1 | 10/2004 | Chew et al. |
| 2004/0249335 A1 | 12/2004 | Faul et al. |
| 2004/0249470 A1 | 12/2004 | Whitmore |
| 2005/0010275 A1 | 1/2005 | Sahatjian et al. |
| 2005/0010280 A1 | 1/2005 | Jing et al. |
| 2005/0021084 A1 | 1/2005 | Lu et al. |
| 2005/0107733 A1 | 5/2005 | Faul et al. |
| 2005/0137707 A1 | 6/2005 | Malek |
| 2005/0149166 A1 | 7/2005 | Schaeffer et al. |
| 2005/0159726 A1 | 7/2005 | Evans et al. |
| 2005/0171598 A1 | 8/2005 | Schaeffer |
| 2005/0192659 A1 | 9/2005 | Dahl et al. |
| 2005/0216074 A1 | 9/2005 | Sahatjian et al. |
| 2005/0228413 A1 | 10/2005 | Binmoeller |
| 2005/0273060 A1* | 12/2005 | Levy ................... A61B 17/1114 604/192 |
| 2005/0277964 A1 | 12/2005 | Brenneman et al. |
| 2005/0277965 A1 | 12/2005 | Brenneman et al. |
| 2006/0047337 A1 | 3/2006 | Brenneman |
| 2006/0058864 A1 | 3/2006 | Schaeffer et al. |
| 2006/0085034 A1 | 4/2006 | Bettuchi |
| 2006/0106455 A1 | 5/2006 | Furst et al. |
| 2006/0129221 A1 | 6/2006 | Heruth |
| 2006/0135963 A1 | 6/2006 | Kick et al. |
| 2006/0155369 A1 | 7/2006 | Edwin et al. |
| 2006/0235269 A1 | 10/2006 | Waxman |

(56) References Cited

U.S. PATENT DOCUMENTS

| | | |
|---|---|---|
| 2006/0247575 A1 | 11/2006 | Cartledge et al. |
| 2007/0016306 A1 | 1/2007 | Dua et al. |
| 2007/0021828 A1 | 1/2007 | Krolik et al. |
| 2007/0038283 A1 | 2/2007 | Mustapha |
| 2007/0043391 A1 | 2/2007 | Moszner et al. |
| 2007/0055358 A1 | 3/2007 | Krolik et al. |
| 2007/0067011 A1 | 3/2007 | Krolik et al. |
| 2007/0073376 A1 | 3/2007 | Krolik et al. |
| 2007/0073388 A1 | 3/2007 | Krolik et al. |
| 2007/0088425 A1 | 4/2007 | Schaeffer |
| 2007/0173867 A1 | 7/2007 | Brenneman |
| 2007/0173921 A1 | 7/2007 | Wholey et al. |
| 2007/0179592 A1 | 8/2007 | Schaeffer |
| 2007/0225634 A1 | 9/2007 | Ferren et al. |
| 2007/0249985 A1 | 10/2007 | Brenneman et al. |
| 2007/0293940 A1 | 12/2007 | Schaeffer et al. |
| 2008/0195171 A1 | 8/2008 | Sharma |
| 2008/0243151 A1 | 10/2008 | Binmoeller et al. |
| 2009/0143713 A1 | 6/2009 | Van Dam et al. |
| 2009/0143759 A1 | 6/2009 | Van Dam et al. |
| 2009/0143760 A1 | 6/2009 | Van Dam et al. |
| 2009/0306633 A1 | 12/2009 | Trovato et al. |
| 2011/0054381 A1 | 3/2011 | Van Dam et al. |
| 2011/0071350 A1 | 3/2011 | Van Dam et al. |
| 2011/0071566 A1 | 3/2011 | Dam et al. |

FOREIGN PATENT DOCUMENTS

| | | |
|---|---|---|
| EP | 1044663 A2 | 10/2000 |
| EP | 1044663 A3 | 3/2001 |
| EP | 1314404 A2 | 5/2003 |
| EP | 1314404 A3 | 9/2003 |
| EP | 1795151 A1 | 6/2007 |
| GB | 2460287 A | 11/2009 |
| JP | 03-9746 A | 1/1991 |
| JP | 11076412 | 3/1999 |
| JP | 15-116982 | 4/2003 |
| RU | 2226364 C1 | 4/2004 |
| SU | 620262 | 8/1978 |
| SU | 688185 | 9/1979 |
| SU | 1131498 | 12/1984 |
| SU | 1586687 | 8/1990 |
| SU | 1634257 | 3/1991 |
| SU | 1828745 | 7/1993 |
| WO | WO 96/13296 A1 | 5/1996 |
| WO | WO 97/27898 A1 | 8/1997 |
| WO | WO 00/12832 A2 | 3/2000 |
| WO | WO 00/18325 A1 | 4/2000 |
| WO | WO 00/12832 A3 | 6/2000 |
| WO | WO 01/58384 A1 | 8/2001 |
| WO | WO 2004/069097 A2 | 8/2004 |
| WO | WO 2006/062996 A2 | 6/2006 |
| WO | WO 2006/127784 A2 | 11/2006 |
| WO | WO 2007/005010 A1 | 1/2007 |
| WO | WO 2007/014283 A2 | 2/2007 |
| WO | WO 2006/127784 A3 | 5/2007 |
| WO | WO 2007/050628 A2 | 5/2007 |
| WO | WO 2007/050628 A3 | 1/2008 |
| WO | WO 2006/062996 A3 | 4/2009 |
| WO | WO 2007/014283 A3 | 4/2009 |
| WO | WO 2009/073507 A2 | 6/2009 |
| WO | WO 2009/073507 A3 | 6/2009 |
| WO | WO 2009/073515 A2 | 6/2009 |
| WO | WO 2009/073515 A3 | 6/2009 |
| WO | WO 2009/073521 A2 | 6/2009 |
| WO | WO 2009/073521 A3 | 6/2009 |
| WO | WO 2012/071031 A1 | 5/2012 |

OTHER PUBLICATIONS

Non-Final Office Action in U.S. Appl. No. 13/410,281 dtd Oct. 28, 2013 (11 pages).
Non-final Office Action received on U.S. Appl. No. 12/951,803 dated Jan. 17, 2012.
British Search Report received for British Appln. No. 0821930.5 dated Mar. 19, 2009.
European Supplementary Search Report received for EP 08856414.1 completed Feb. 22, 2012.
Final Office Action received for U.S. Appl. No. 12/277,443 dated Jun. 21, 2010.
International Search Report and Written Opinion received for PCT/US2008/084830 dated Jun. 24, 2009.
International Search Report and Written Opinion received for PCT/US2008/084865 dated Jun. 24, 2009.
International Search Report and Written Opinion received for PCT/US2008/084888 dated Jul. 17, 2009.
Non-final Office Action received for U.S. Appl. No. 12/277,443 dated Oct. 22, 2009.
Non-final Office Action received for U.S. Appl. No. 12/959,264 dated Sep. 12, 2011.
Non-final Office Action received in U.S. Appl. No. 13/410,281 dated Jan. 17, 2013.
Non-Final Office Action in U.S. Appl. No. 12/951,803 dtd Jan. 2, 2014 (11 pages).
Final Office Action in U.S. Appl. No. 12/951,803 dtd Jul. 19, 2013.
US Office Action on U.S. Appl. No. 12/951,803 Dtd Feb. 25, 2015.
US Office Action on U.S. Appl. No. 13/410,281 Dtd Feb. 24, 2015.
Final Office Action received for U.S. Appl. No. 12/951,803 dated Aug. 26, 2014.
Final Office Action received for U.S. Appl. No. 13/410,281 Dtd Mar. 10, 2014.
Non-final Office Action received for U.S. Appl. No. 13/410,281 dated Sep. 12, 2014.
Extended European Search Report for Patent Application No. 08856414.1, mailed Feb. 29, 2012.
International Search Report and Written Opinion in International Application No. PCT/US2010/057736 mailed Feb. 28, 2012.

* cited by examiner

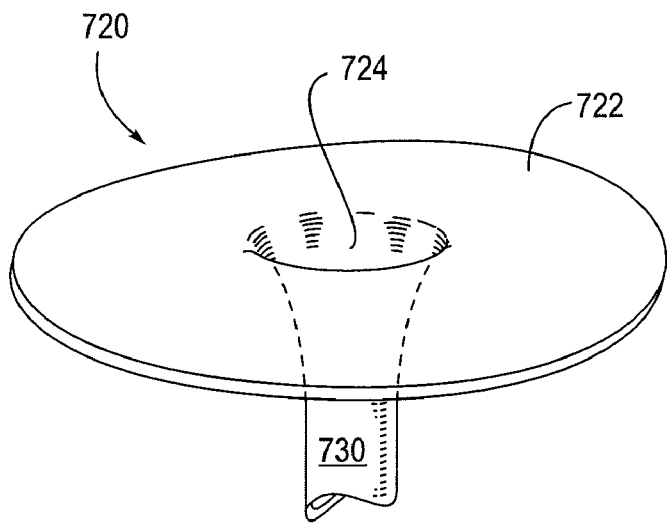
FIG. 7C(1)
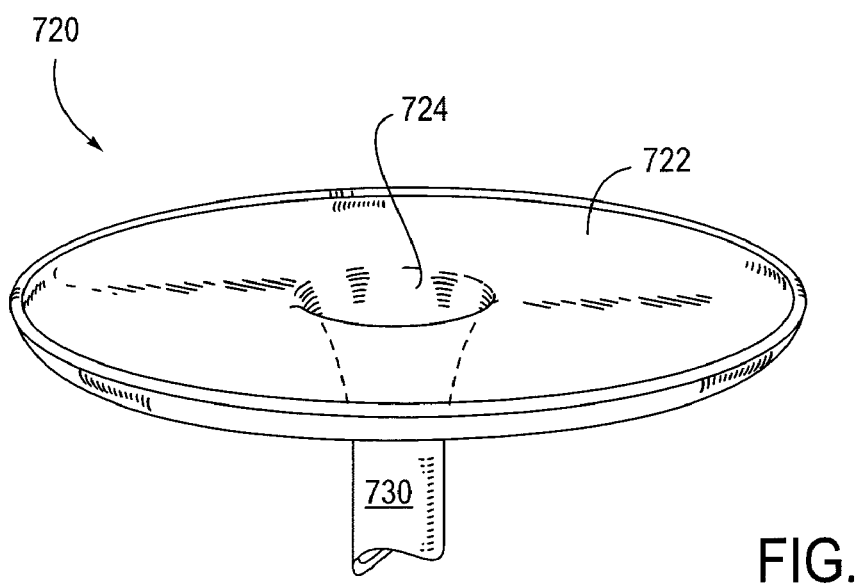
FIG. 7C(2)

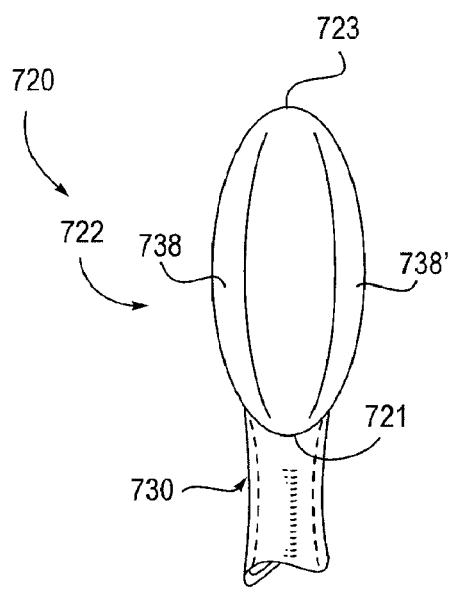
FIG. 7D(1)
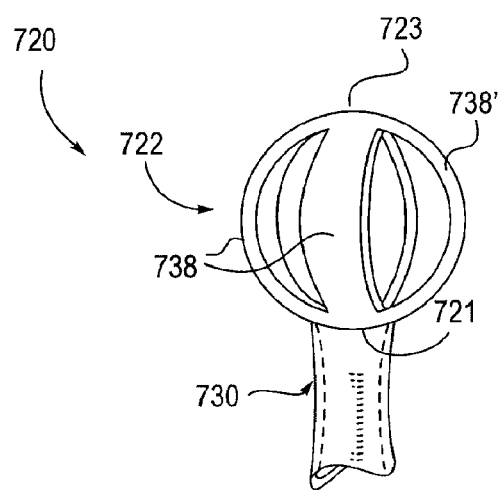
FIG. 7D(2)
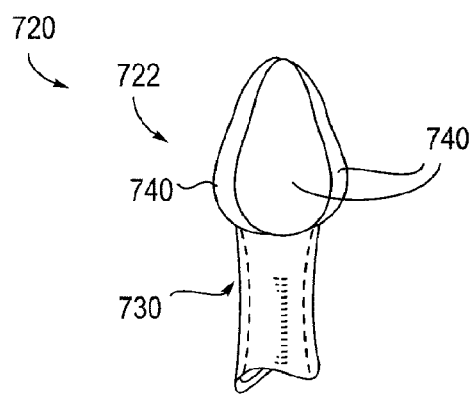
FIG. 7E(1)
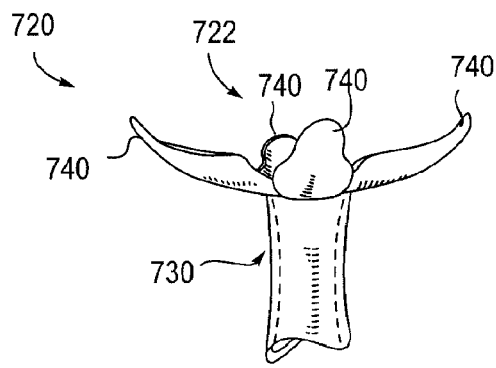
FIG. 7E(2)

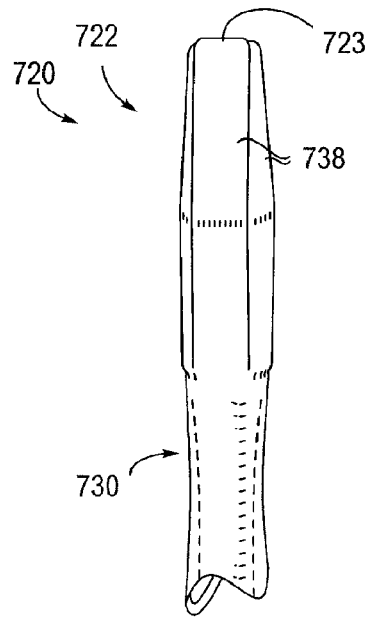
FIG. 7F(1)
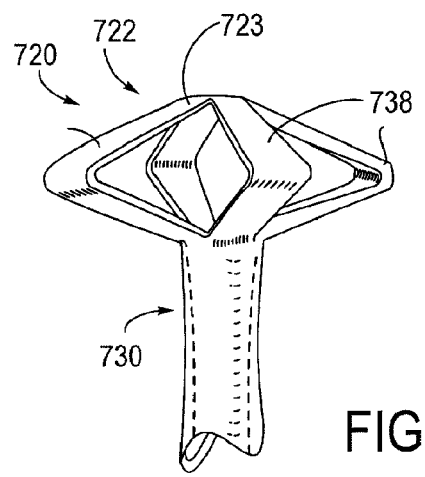
FIG. 7F(2)
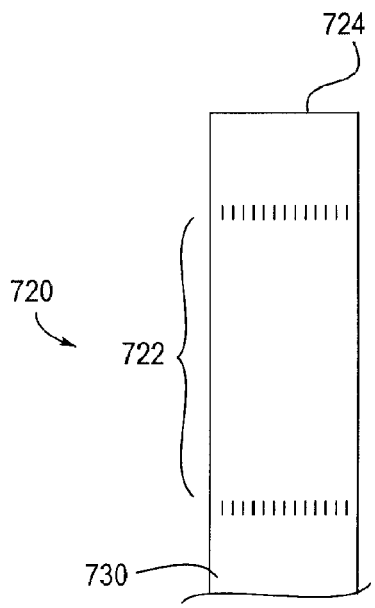
FIG. 7G(1)
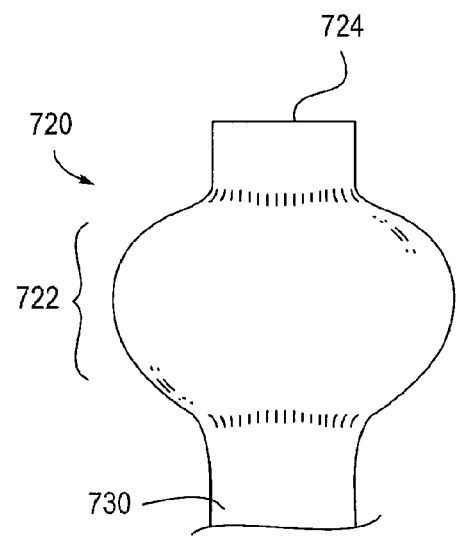
FIG. 7G(2)

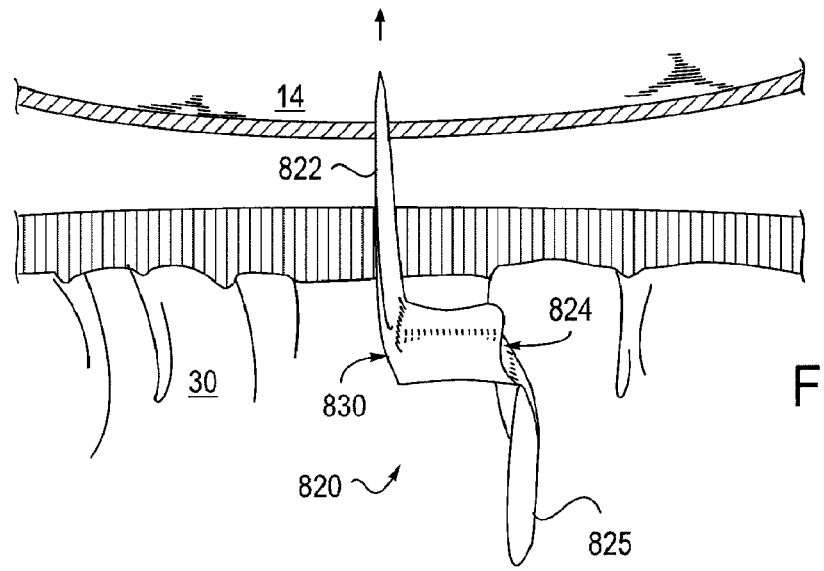
FIG. 8A(1)
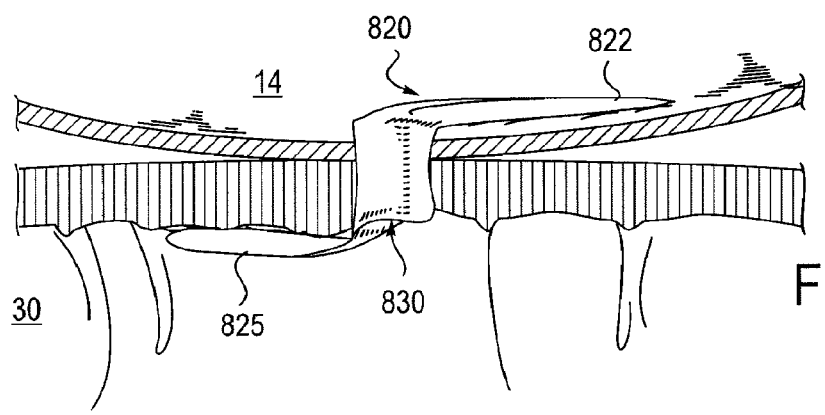
FIG. 8A(2)
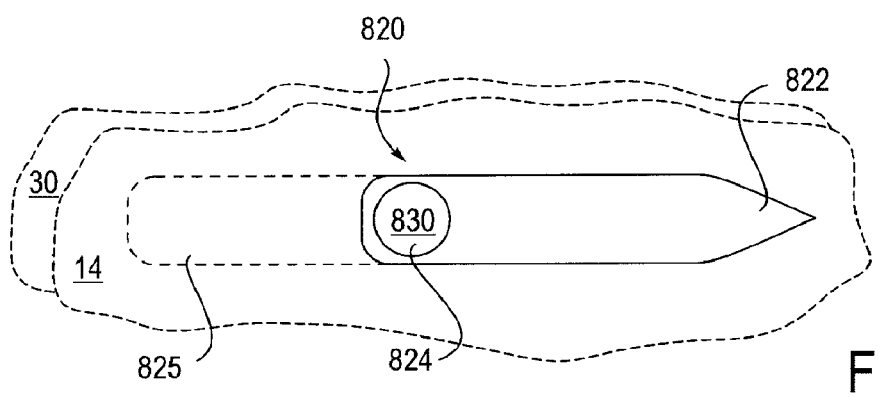
FIG. 8A(3)

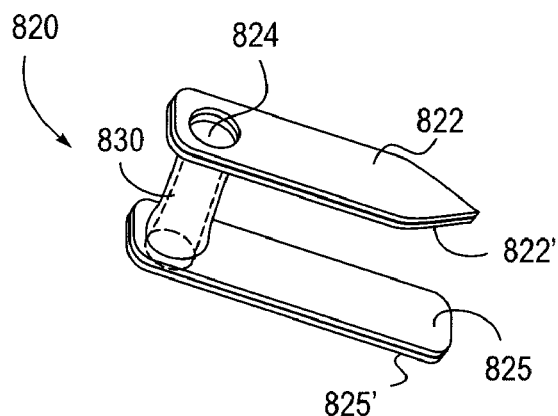
FIG. 8B(1)
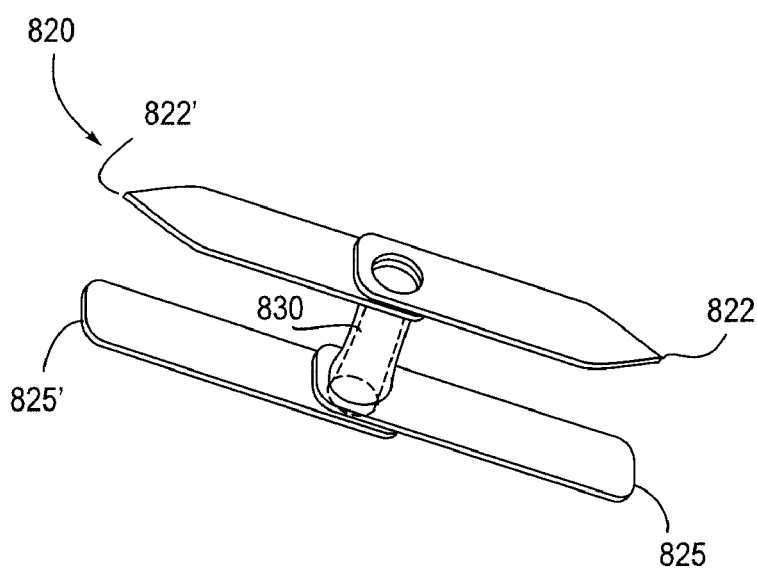
FIG. 8B(2)

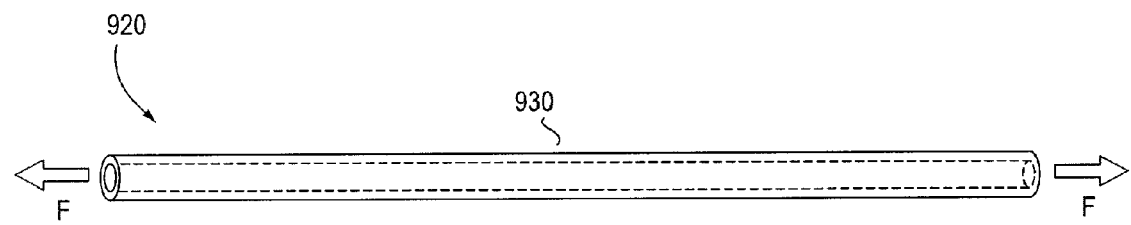
FIG. 9A(1)
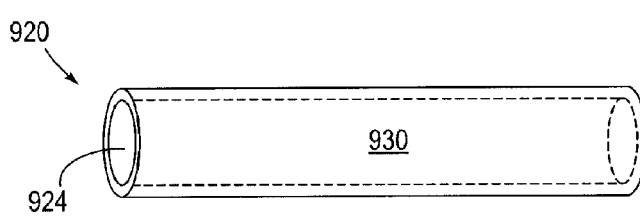
FIG. 9A(2)
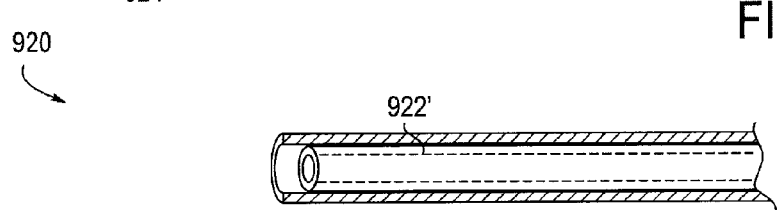
FIG. 9A(3)
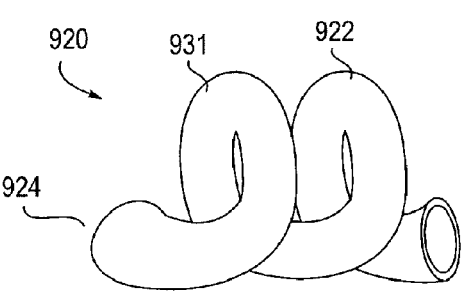
FIG. 9B
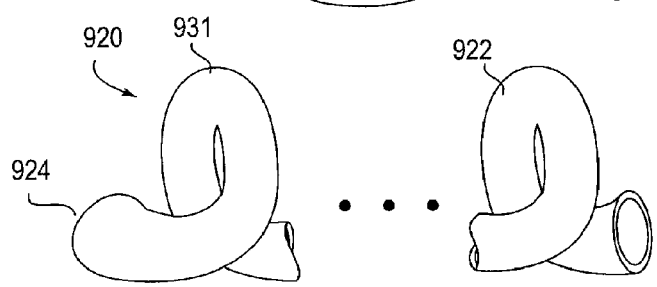
FIG. 9C

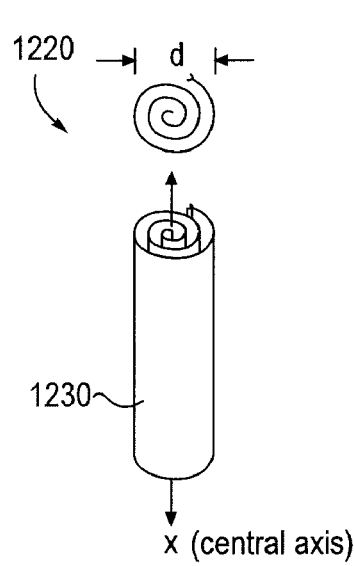
FIG. 12A(1)
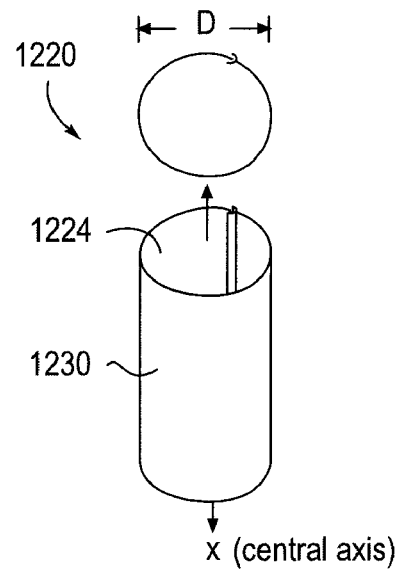
FIG. 12A(2)
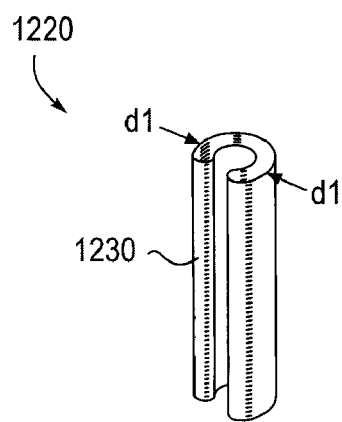
FIG. 12B(1)
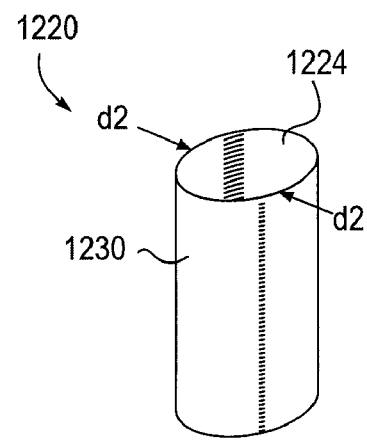
FIG. 12B(2)

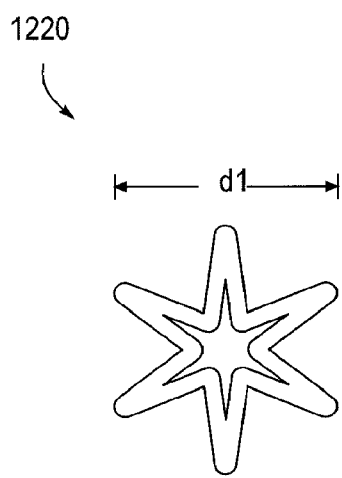
FIG. 12C(1)
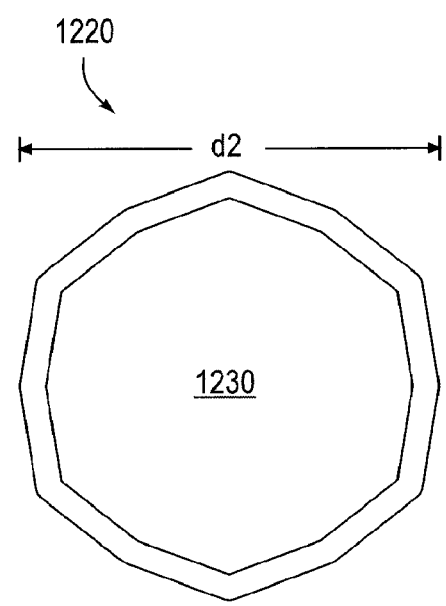
FIG. 12C(2)

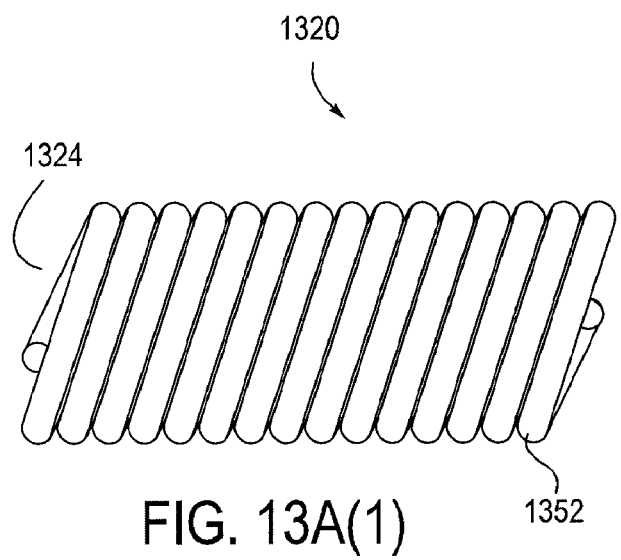 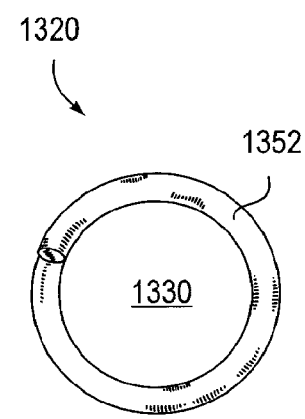
FIG. 13A(1)    FIG. 13A(2)
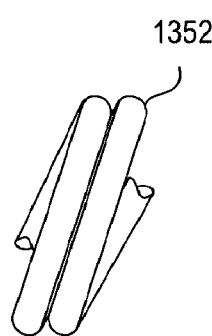 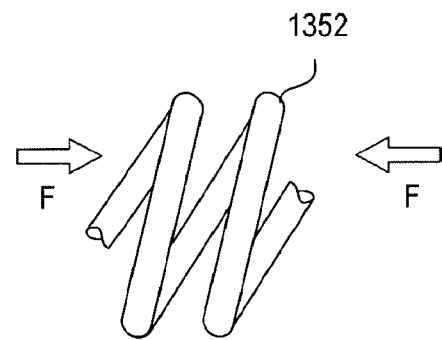
FIG. 13B(1)    FIG. 13B(2)

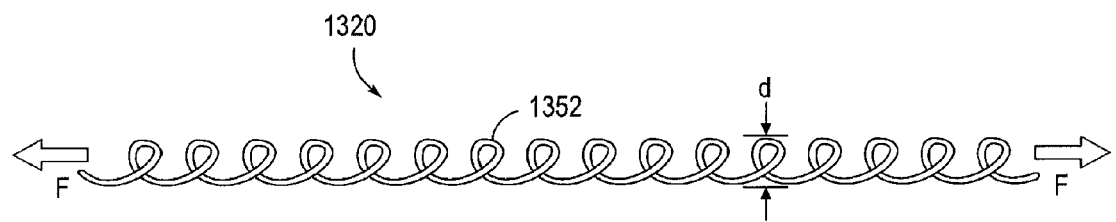
FIG. 13C(1)
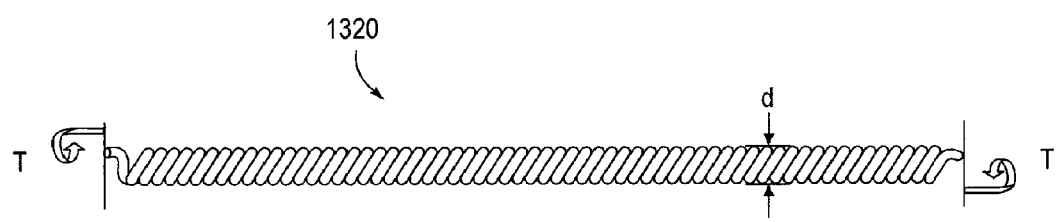
FIG. 13C(2)

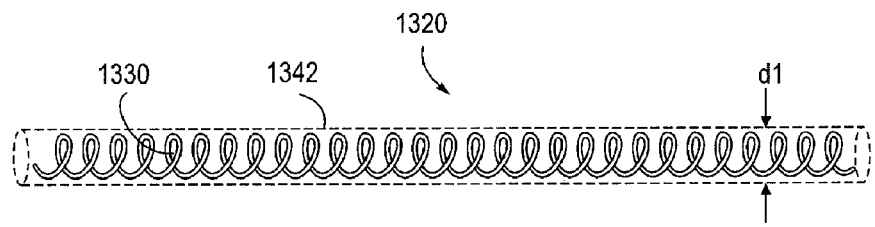
FIG. 13D
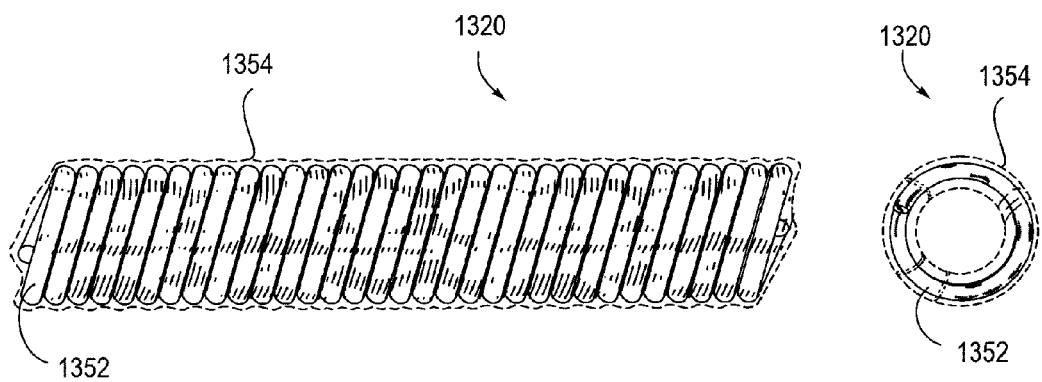
FIG. 13E(1)   FIG. 13E(2)

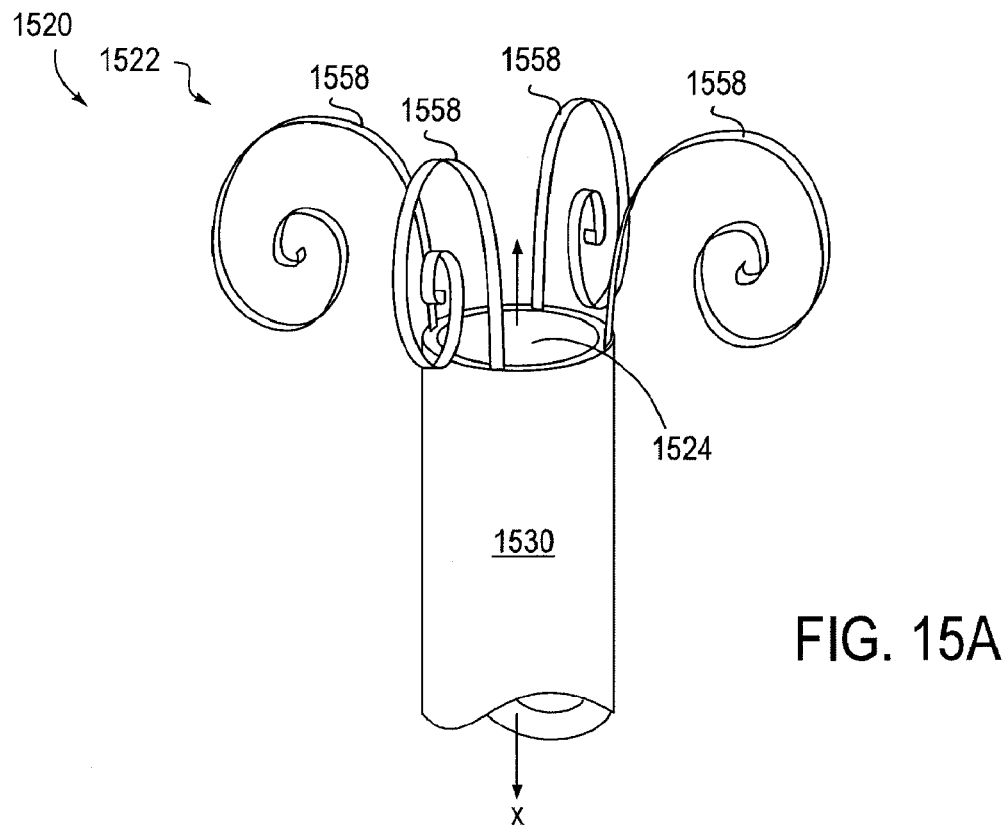
FIG. 15A
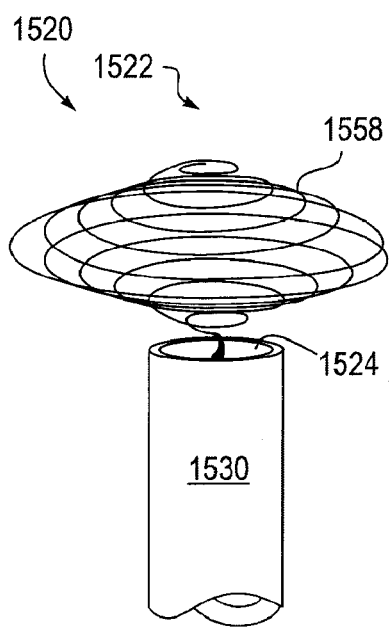
FIG. 15B(1)
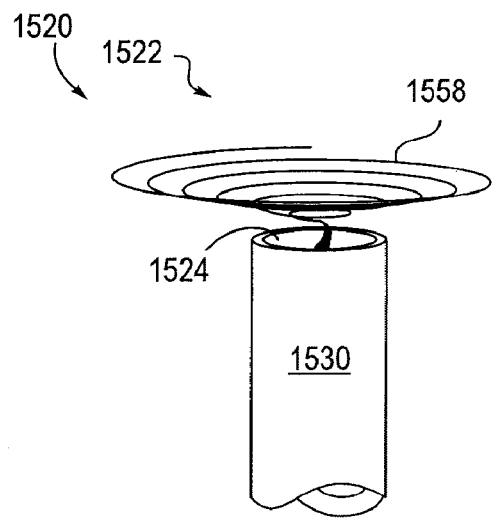
FIG. 15B(2)

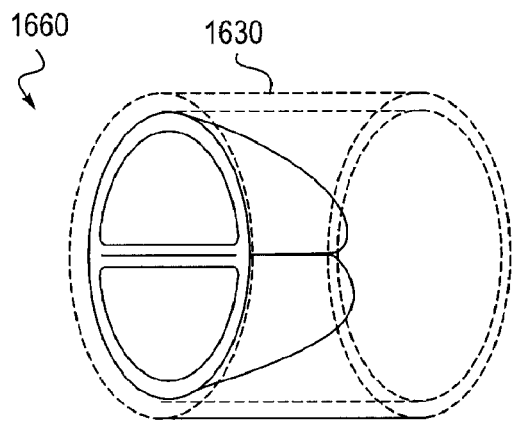
FIG. 16D(1)
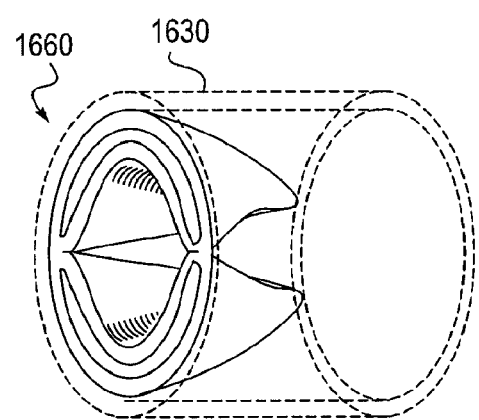
FIG. 16D(2)
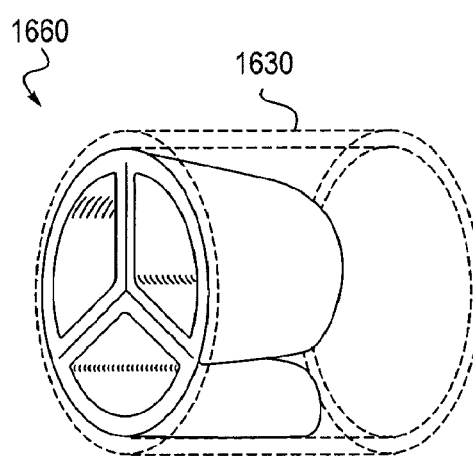
FIG. 16E(1)

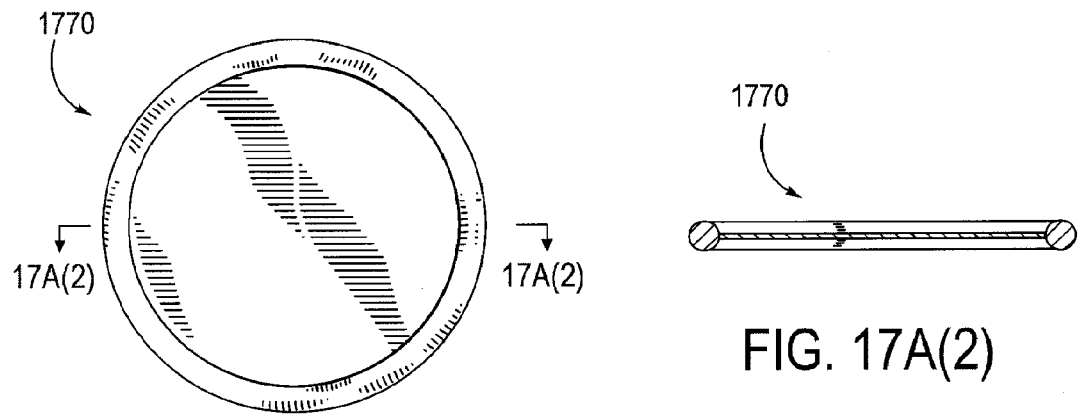
FIG. 17A(1)
FIG. 17A(2)
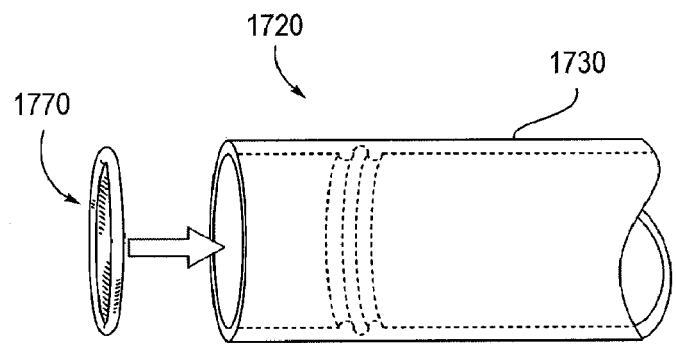
FIG. 17B

BILIARY SHUNTS, DELIVERY SYSTEMS, METHODS OF USING THE SAME AND KITS THEREFOR

CROSS-REFERENCE

This application is a continuation of application serial no. 12/277,491, filed Nov. 25, 2008, now abandoned which claims the benefit of U.S. Provisional Application No. 60/991,682, filed Nov. 30, 2007, and application Ser. No. 61/033,368 filed Mar. 3, 2008, which applications are incorporated herein by reference.

This application has related subject matter to U.S. Utility Patent Application No. 12/277,338, filed Nov. 25, 2008, entitled "Methods, Devices, Kits and Systems for Defunctionalizing the Cystic Duct" by Jacques Van Dam, J. Craig Milroy, and R. Matthew Ohline and U.S. Utility Patent Application No. 12/277,443, filed Nov. 25, 2008, entitled, "Methods, Devices, Kits and Systems for Defunctionalizing the Gallbladder" by Jacques Van Dam, J. Craig Milroy, and R. Matthew Ohline, which applications are incorporated herein by reference.

FIELD OF THE INVENTION

The invention described in this patent application addresses challenges confronted in the treatment of biliary disease. Biliary disease includes conditions affecting the gallbladder, cystic duct, and common bile duct.

Biliary System Function and Anatomy:

Bile is a greenish-brown digestive fluid produced by the liver 10 illustrated in FIG. 1, and is vital for the digestion of fatty foods. Bile is secreted by liver cells and collected by a network of ducts that converge at the common hepatic duct 12. While a small quantity of bile drains directly into the lumen of the duodenum 30 (the section of small intestine immediately downstream of the stomach), most travels through the common hepatic duct 12 and accumulates in the lumen of the gallbladder 14. Healthy gallbladders are pear-shaped sacs with a muscular wall that, on average, measure 10 cm in length and can store approximately 50 ml of fluid within its lumen. When fatty foods are ingested, the hormone cholecystokinin is released, which causes the gallbladder 14 to contract. Contraction of the gallbladder 14 forces bile to flow from the gallbladder 14, through the cystic duct 16, into the common bile duct 18, out the papilla 28, and finally into the duodenum 30 of the small intestine. Here, it mixes and reacts with the food that exits the stomach. The Sphincter of Oddi 26 controls secretions from the liver, pancreas 24, and gallbladder 14 into the duodenum 30 of the small intestine. The opening on the inside of the descending duodenum 30 after the Sphincter of Oddi 26 is called the major duodenal papilla 28 (of Vater). Together, the biliary ducts, the gallbladder 14, the cystic duct 16 and the common bile duct 18 comprise the biliary system (FIG. 1).

The pancreas 24 is a gland organ in the digestive and endocrine system of vertebrates. It is both an endocrine gland (producing several important hormones, including insulin, glucagon, and somatostatin), as well as an exocrine gland, secreting pancreatic juice containing digestive enzymes that pass to the small intestine. These enzymes help in the further breakdown of the carbohydrates, protein, and fat in the chyme. The pancreatic duct 22, or duct of Wirsung, is a duct joining the pancreas 24 to the common bile duct 18 to supply pancreatic juices which aid in digestion provided by the exocrine pancreas. The pancreatic duct 22 joins the common bile duct 18 just prior to the major duodenal papilla 28, after which both ducts perforate the medial side of the second portion of the duodenum 30 at the major duodenal papilla.

Biliary Disease:

The most common problem that arises in the biliary system is the formation of gallstones, a condition called cholelithiasis. Approximately 20 million Americans have gallstones, and about 1-3% will exhibit symptoms in any given year. In the U.S., gallstones are more common among women, with 25% of women having gallstones by the age of 60 and 50% by the age of 75. Pregnancy and hormone replacement therapy increase the risk of forming gallstones. Prevalence is lower for American men: approximately 25% will develop gallstones by the age of 75. In the U.S., gallstones are responsible for the highest number of hospital admissions due to severe abdominal pain.

Gallstones 20, 20' are most often composed of cholesterol, but may also be formed from calcium bilirubinate, in which case they are called pigment stones. They range in size from a few millimeters to several centimeters, and are irregularly shaped solids resembling pebbles. They can form in the gallbladder 14, cystic duct 16, and/or the common bile duct 18 (FIG. 2). By themselves, gallstones 20 do not necessarily result in disease states. This is the case 90% of the time. However, stones can cause infection and inflammation, a condition known as cholecystitis, which is generally the result of restricting or blocking the flow of bile from the gallbladder 14 and common bile duct 18, or the fluids secreted by the pancreas 24.

Gallbladder disease may be chronic, and patients who suffer from this may periodically experience biliary colic. Symptoms include pain in the upper right abdomen near the ribcage, nausea, and/or vomiting. The pain may resolve within an hour of onset, may prove unresponsive to over-the-counter medicines, and may not decrease with changes of position or the passage of gas. Recurrence is common, with pain often recurring at the same time of day, but with frequency of less than once per week. Fatty or large meals may cause recurrence several hours after eating, often awakening the patient at night. Patients may elect to suffer from these symptoms for very long periods of time, such as years or even decades.

Patients with chronic cholecystitis have gallstones and low-grade inflammation. Untreated, the gallbladder 14 may become scarred and stiff over time, leading to a condition called dysfunctional gallbladder. Patients who have chronic cholecystitis or dysfunctional gallbladder may experience gas, nausea, and abdominal discomfort after meals, and chronic diarrhea.

Acute cholecystitis (a surgical emergency) develops in 1-3% of those with symptomatic gallstone disease, and is due to obstruction of the common bile duct 18 or cystic duct 16 by stones or sludge. Symptoms are similar to biliary colic, though they are more severe and persistent. Pain in the upper right abdomen can be constant and severe, the intensity may increase when drawing breath, and it may last for days. Pain may radiate to the back, under the breastbone or the shoulder blades, and it may be perceived on the left side of the abdomen. In addition to nausea and vomiting, one third of patients experience fever and chills. Complications from acute cholcystitis can be serious and life threatening, and include gangrene, abscesses, perforation of the gallbladder 14 which can lead to bile peritonitis, pus in the gallbladder wall (empyema), fistulae, and gallstone ilius (when a gallstone creates a blockage in the small intestine).

When gallstones 20' become lodged in the common bile duct 18 (FIG. 2), the condition is known as choledocholithiasis. Symptoms for this condition include pain, nausea and vomiting, and some patients develop jaundice, have dark urine and/or lighter stools, rapid heartbeat, and experience an abrupt drop in blood pressure. These symptoms can also be accompanied by fever, chills, and/or severe pain in the upper right abdomen. Complications from choledocholithiasis can also be very serious, and include infection of the common bile duct 18 (cholangitis) and inflammation of the pancreas 24 (pancreatitis).

A smaller patient population suffers from gallbladder disease that occurs in the absence of gallstones. This condition, called acalculous gallbladder disease, can also be chronic or acute. Chronic acalculous gallbladder disease, also called biliary dyskinesia, is thought to be caused by motility disorders that affect the gallbladder's ability to store and release bile. Acute acalculous gallbladder disease occurs in patients who suffer from other serious illnesses which can lead to inflammation of the gallbladder 14 because of a reduction in the supply of blood to the gallbladder 14 or a reduced ability to contract and empty bile into the duodenum 30.

Cancer can also develop in the gallbladder 14, though this condition is rare. Gallstones have been found in 80% of patients with gallbladder cancer. Gallbladder cancer typically develops from polyps, which are growths inside the gallbladder 14. When polyps 15 mm across or larger are observed, the gallbladder is removed as a preventive measure. Polyps smaller than 10 mm are widely accepted as posing low risk and are not generally removed. When detected early, before the cancer has spread beyond the mucosa (inner lining) of the gallbladder, the 5-year survival rate is approximately 68%. However, gallbladder cancer is not usually detected until patients are symptomatic, by which time the disease is more advanced.

Treatment of Biliary Disease:

The most effective treatment for biliary disease has been surgical removal of the gallbladder 14, a procedure called cholecystectomy. Surgical removal of the gallbladder 14 is indicated for patients who experience a number of less severe gallstone attacks, cholecystitis, choledocholithiasis, pancreatitis, acalculous biliary pain with evidence of impaired gallbladder 14 emptying, those at high risk for developing gallbladder cancer, and those who have previously undergone endoscopic sphincterotomy for common bile duct stones. Other treatment modalities exist and are frequently used, but gallbladder disease tends to recur in the majority of patients who forgo cholecystectomy and pursue alternatives. Removal of the gallbladder 14 is highly successful at permanently eliminating biliary disease. Cholecystectomy is one of the most commonly performed procedures on women. The gallbladder 14 is not an essential organ, and after a period of adjustment post surgery, patients tend to return to more or less normal digestive function.

Cholecystectomy can be performed either as open surgery, which requires a single larger incision in the upper right abdomen, or laparoscopic surgery, in which several small instruments are inserted through much smaller incisions in the abdomen. Approximately 80% of cholecystectomies are performed laparoscopically. The primary benefits of this minimally invasive approach are faster recovery for the patient, and a reduction in overall healthcare costs. Patients who receive laparoscopic cholecystectomy are usually released the same day. By contrast, patients receiving open cholecystectomies typically spend 5-7 days in a hospital before release. 5-10% of laparoscopic procedures convert to open procedures when difficulties arise, such as injury to major blood vessels, inadequate access, inadequate visualization, previous endoscopic sphincterotomy, and thickened gallbladder wall. Complications from cholecystectomy (open or laparoscopic) include bile duct injuries (0.1-0.5% for open, 0.3-2% with a declining trend for laparoscopic), pain, fatigue, nausea, vomiting, and infection. In up to 6% of cases, surgeons fail to identify and remove all gallstones present.

In some cases, the degree of infection and inflammation prevents patients from undergoing immediate cholecystectomy. In these cases, the gallbladder 14 must be treated with antibiotics and anti-inflammatory agents, and drained through a tube into a reservoir outside the abdomen. Placement of this tube occurs in a procedure called percutaneous cholecystostomy, in which a needle is introduced to the gallbladder 14 through the abdomen, fluid is withdrawn, and a drainage catheter is inserted. This catheter drains into an external bag which must be emptied several times a day until the tube is removed. The drainage catheter may be left in place for up to 8 weeks. In cases where no drainage catheter is inserted, the procedure is called gallbladder aspiration. Since no indwelling catheter is placed, the complication rate for gallbladder aspiration is lower than that of percutaneous cholecystostomy.

Treatment methodologies other than cholecystectomy include expectant management, dissolution therapy, endoscopic retrograde cholangiopanctreatograpy (ERCP) with endoscopic sphincterotomy, and extracorporeal shockwave lithotripsy (ESWL).

Expectant management is appropriate for patients who have gallstones but no symptoms, and for non-emergency cases with less severe symptoms. This approach is not recommended when patients are in high risk categories (e.g. high risk for gallbladder cancer) or have very large gallstones (e.g. greater than 3 cm).

Oral dissolution therapy involves the administration of pills containing bile acids that can dissolve gallstones. This approach is only moderately effective, and the rate of recurrence of gallstones after completion of treatment is high. It is not appropriate for patients with acute inflammation or stones in the common bile duct (more serious conditions). Dissolution therapy tends to be more effective for patients with cholesterol stones, and is sometimes used in conjunction with lithotripsy. Despite its relative ineffectiveness, it is costly: treatment can last up to 2 years and the drugs cost thousands of dollars per year.

Related to oral dissolution therapy is contact dissolution, a procedure that involves injection of a solvent such as methyl tert-butyl ether (MTBE) directly into the gallbladder 14. This approach is highly effective at dissolving gallstones, but patients may experience severe burning pain.

ERCP (endoscopic retrograde cholangiopancreatograpy) is a procedure in which an endoscope is introduced through the mouth of a patient, past the stomach to the papilla 28, where the common bile duct 18 empties into the duodenum 30. The overall goal of the procedure is to insert instruments and tools into the common bile duct 18 via the papilla 28 in order to treat biliary disease. Typically, endoscopic sphincterotomy is performed, which is a procedure that enlarges the opening of the papilla 28 in the small intestine. This can be accomplished surgically or via balloon dilation. Contrast agent is introduced into the common bile duct 18 to visualize the biliary tree fluoroscopically. Tools for clearing blockages, such as mechanical lithotripsy devices, can be deployed to crush gallstones and remove the resulting debris. Drainage catheters and stents may also be inserted to facilitate the drainage of bile past obstructions. Complications from this challenging procedure occur at a rate of 5-8%, and include recurrence of stone formation, pancreatitis, infection, bleeding, and perforation.

Extracorporeal shockwave lithotripsy (ESWL) is a technique in which focused, high-energy ultrasound is directed at the gallbladder 14. The ultrasound waves travel through the soft body tissue and break up the gallstones. The resulting stone fragments are then usually small enough to pass through the bile duct into the small intestine. Oral dissolution therapy is often used in conjunction with ESWL. This treatment is not in common use, as less than 15% of the patient population are good candidates. However, ESWL is used to treat patients who are not candidates for surgery. Complications from ESWL include pain in the gallbladder area, pancreatitis, and failure of the gallstone fragments to pass into the small intestine.

SUMMARY OF THE INVENTION

An aspect of the invention is directed to devices for treating biliary disease. Suitable devices comprise: a component configured for deployment between a gallbladder and a location within a gastrointestinal tract of a patient, the component having a proximal end and a distal end and a lumen extending therethrough. The devices can be configured for deployment by an endoscope, a needle, a guidewire, a guidance catheter, and/or a dilatation balloon. Endoscopes can further be adapted to comprise an ultrasound device. A system for treating biliary disease is also contemplated which comprises a device for configuring a duct between a gallbladder and a gastrointestinal tract of a patient having a proximal end and a distal end with a lumen extending therethrough between. In some aspects the devices can be configured to further comprise a delivery mechanism for delivering a substance. Deployment of these devices can, in some instances, cause a conduit to be formed between a gallbladder lumen and a target location within the gastrointestinal tract.

Another aspect of the invention is directed to a biliary disease treatment device comprising: an implant adapted to be delivered by an endoscope to a gastrointestinal site in proximity to a gallbladder, and further adapted to form a conduit between the gastrointestinal site and the gallbladder. The conduit can, for example, be formed between a lumen of the gallbladder and a target location within the gastrointestinal tract, such as proximal to a duodenum.

Devices according to any one of the configurations disclosed can be formed from a bioresorbable material. Moreover, the devices can be removable and/or expandable. The devices can also be configurable in one or more configurations selected from a deployment configuration, a delivery configuration and a final configuration. Moreover, the devices can be configured such that a profile of the device changes between said configurations. Additionally, or in the alternative, a cross-sectional area of the device can be variable along a length of the devices. In some configurations a component or implant can be configured such that it has a flareable end, suitable flareable ends include ends that are generally hemispherical. Additionally, components or implants can comprise a configurable retainable feature. In some aspects, components or implants can comprise one or more clips configured to secure the components or implants at one or more positions. In some configurations, one or more fenestrations may be provided. Moreover, the lumen or conduit can be configurable to provide restrictable fluid flow or to provide for a valve, such as a flow-restrictor or one-way valve. Any of the configurations of the device can be constructed such that the device is flexible. The system or device can also be configured to include a generally elongate tube that is adapted and configured to extend into the gastrointestinal tract. Configurations that include an elongate tube can be configured such that the tube is patent at a first end; the patent first end can be for placement adjacent the gallbladder. In still other configurations, the elongate tube is not patent at a second end. Moreover, the tube can be configured such that it has an adjustable length. Additionally, one or more fluid control components can be provided to the designs. Additionally, an enlargeable portion comprising two or more legs can be provided.

Another aspect of the invention is directed to a kit for treating biliary disease comprising a duct forming component positioned between a gallbladder and a gastrointestinal tract. The kit can comprise any of the devices or systems described herein. Additionally, compounds can be provided for delivery to a tissue. Compounds or materials include, but are not limited to, for example, one or more of each of sclerosing agents, antibiotics, inflammatory agents, anti-inflammatory agents, biocompatible gels, and biocompatible foams. Additionally, a catheter, guidewire, needle, guidance catheter or balloon catheter can be provided. In some aspects, the kit can also include an ablation device. Additional components of the kits include, for example, one or more of each of a pair of scissors, a scalpel, a swab, a syringe, a hemostat, a lubricant, a needle, a snare, an antiseptic, and an anesthetic.

Yet another aspect of the invention is directed to a method for treating biliary disease. A method of treating biliary disease comprises: (a) creating a duct or fistula between a gallbladder lumen and a portion of a gastrointestinal tract; and (b) providing for drainage from the gallbladder to the gastrointestinal tract. Additionally, the method can comprise the step of delivering a substance to the gallbladder via the duct. Additional method steps include delivering a device to the gallbladder through the duct. Suitable devices to be delivered include one or more of a stent, a drug-coated stent, a catheter, a needle, a guidance catheter, a balloon dilatation catheter and/or a guidewire. In some cases, the step of creating the duct further comprises the step of inserting a device in communication between the gastrointestinal tract and the gallbladder lumen. The step of creating the duct between a gallbladder lumen and a portion of a gastrointestinal tract can further comprise the step of inserting a conduit between the gallbladder lumen and the portion of the biliary system. In some aspects, the method further comprises the step of forming a biological duct in situ from a patient's tissue. As will be appreciated by those skilled in the art, the step of inserting a conduit between the gallbladder lumen and the portion of the gallbladder tract can occur at a first time and the step of forming the biological duct in situ from the patient's tissue occurs at a second time remote from the first time. Moreover the methods can further comprise the step of providing a seal to prevent fluid from leaking into a peritoneum. Additionally the gallbladder can be defunctionalized in situ, such as by delivering a substance or material into a space within the gallbladder. Suitable substances or materials include, but are not limited to, gels and foams. In some instances, the delivered substances can be activated in situ. Additionally, an amount of material can be delivered to fill, or substantially fill, the gallbladder lumen. Additionally, in some instances, the step of defunctionalizing is achieved by one or more of sclerosing or necrotizing a tissue within the gallbladder which can, for example, be achieved by an ablation technique.

Still another aspect of the invention is directed to a method of delivering a device to treat biliary disease comprising: (a) using an endoscope to place a guidewire between an access lumen in a body and a gallbladder; (b) inserting a delivery catheter over the guidewire and into the gallbladder; (c) delivering a conduit on the catheter; and (d) positioning the conduit between the access lumen in the body and the gallbladder to create a lumen therebetween. The methods can also include the step of forming a biological duct in situ from a patient's tissue. Additionally, the step of positioning the conduit can occur at a first time and the step of forming the biological duct in situ from the patient's tissue occurs at a second time remote from the first time. Some methods can further comprise the step of passively retaining a distal end of the guidewire in the gallbladder while the guidewire is used to deliver additional elements. In some instances, the methods include the step of retaining a distal end of the guidewire within the gallbladder. In some methods, gallstones are removed through the created lumen. In other methods, a substance is delivered to the gallbladder via the created lumen. In some instances, the substance occupies the gallbladder lumen and can be one or more of antibiotics, inflammatory agents, and anti-inflammatory agents. Methods may also include preventing bile from entering the or a gallbladder lumen. Additionally, the gallbladder may be localized via endoscopic ultrasound, in some instances. Moreover, it may be useful to access the gallbladder via the gastrointestinal tract. A suitable location for accessing the gallbladder via the gastrointestinal tract would be to access the gallbladder at a duodenum. With any of the methods it may be desirable to alter and/or remove gallstones. Moreover, other obstructions within the biliary system can also be removed. The delivered conduit can be, for example, one or more of a stent, and a drug-coated stent. In some applications of the methods, biliary disease is treated without removal of the gallbladder. In still other applications of the method, a treatment area is visualized as part of the method. In some methods, the conduit is anchored in place. In still other methods, the conduit is changed from a delivery configuration to a deployment configuration, from a delivery configuration to a final configuration or from a deployment configuration to a final configuration. Still other methods provide for reducing a cross-sectional profile of the conduit, providing a seal to prevent fluid from leaking into a peritoneum, and/or restricting fluid flow from the gallbladder lumen to the gastrointestinal tract. Other methods include operating a valve to restrict fluid flow.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention will be set forth with particularity in any claims presented based on this application. A better understanding of the features and advantages of the present invention will be obtained by reference to the following detailed description that sets forth illustrative embodiments, in which the principles of the invention are utilized, and the accompanying drawings of which:

FIGS. 7A-G illustrate variations of retaining features;

FIGS. 8A-B illustrate another variation of a retaining feature;

FIGS. 9A-C illustrates a delivery configuration which reduces cross-sectional area;

FIGS. 12A-C illustrate an alternate embodiment formed from shape memory material;

FIGS. 13A-G illustrate a close-wound spring embodiment of the device;

FIGS. 15A-B illustrate retaining features;

FIGS. 16A-E illustrate a variety of valve embodiments;

FIGS. 17A-B illustrate a variety of plug embodiments;

DETAILED DESCRIPTION OF THE INVENTION

Devices, systems, methods and kits provided herewith can obviate the need for a plurality of procedures, including, for example: 1) percutaneous cholecystostomy, 2) cholecystectomy, 3) percutaneous trans-hepatic cholangiography (PTHC), and 4) endoscopic retrograde cholangiopancreatography (ERCP). Additionally, disclosed treatment modalities enable treatment of a distal common bile duct 18 obstruction, e.g. secondary to pancreatic carcinoma, cholagiocarcinoma, and/or ampullary carcinoma. As will be appreciated by those skilled in the art, the conventional standard of care for treating biliary disease has been surgical removal of the gallbladder 14 and closure of the cystic duct 16. While this has proven to be an effective mechanism for permanently eliminating biliary disease and its recurrence, the present invention seeks to accomplish the same end in a less invasive and less costly way. This may be achieved by treating biliary disease without requiring the removal of the gallbladder 14. Methods and apparatus are described in this application that are intended to effectively treat biliary disease with the gallbladder 14 and cystic duct 16 left in situ by providing a shunt to the gallbladder.

Figure 3:
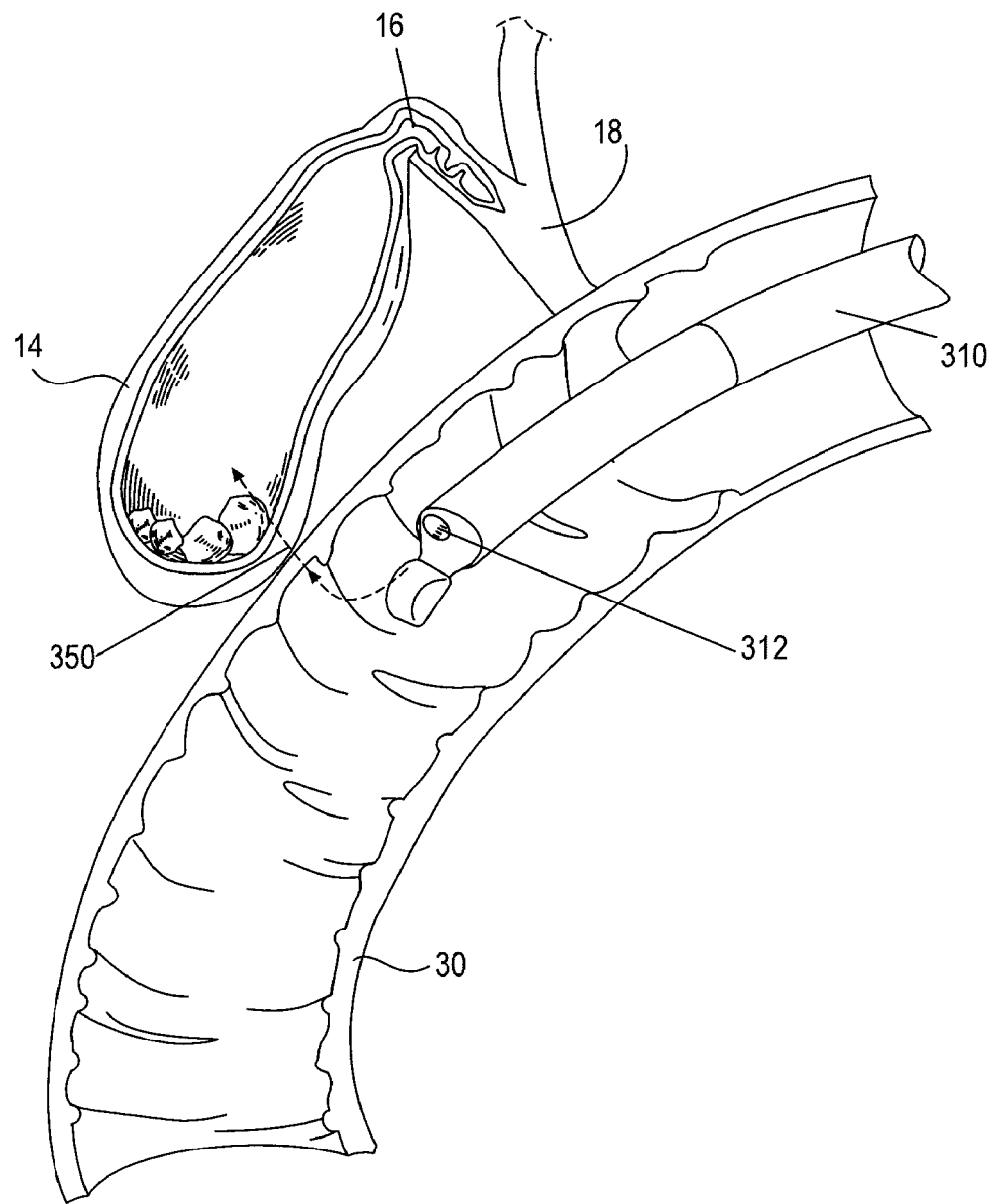
FIG. 3 illustrates an endoscope accessing the biliary system via the intestinal system.
Figure 4A:
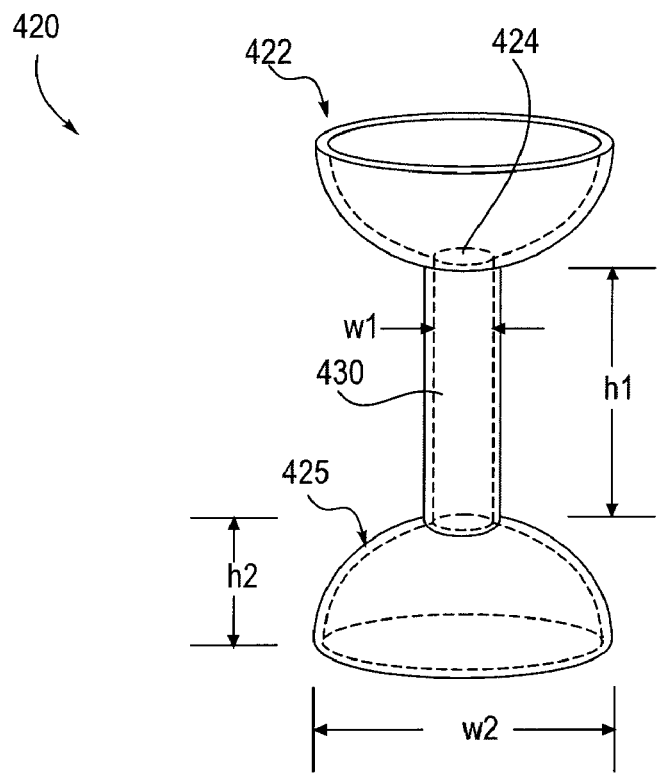
FIGS. 4A-D illustrate embodiments of a device adapted to provide a conduit between two body lumens.
Figure 4B:
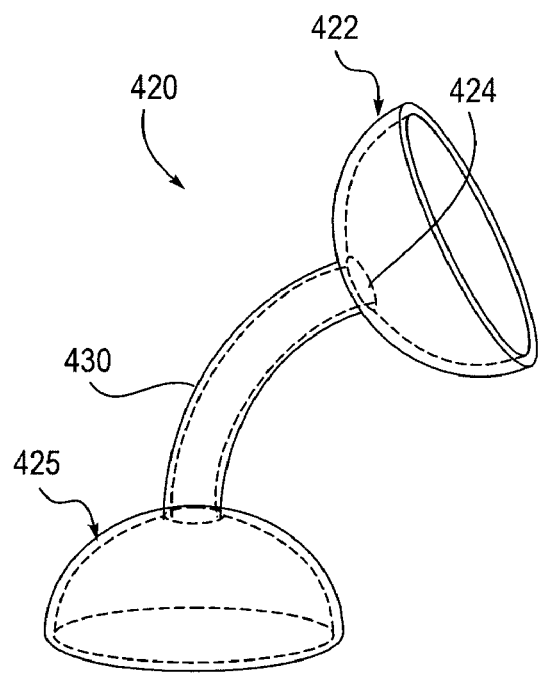
Figure 4C:
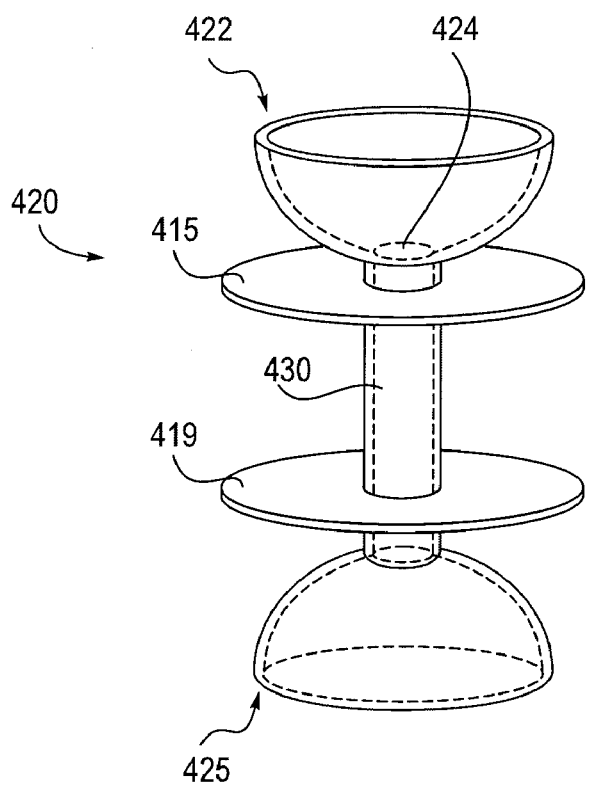
Figure 4D:
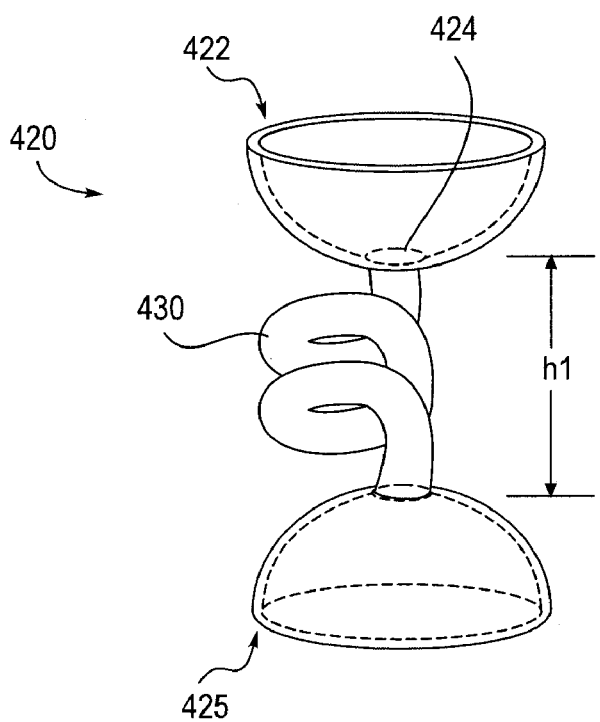

A method of treating biliary disease involves using an endoscope 310 to access a region 350 in the gastrointestinal (GI) tract (FIG. 3) to which the gallbladder 14 is in close proximity, locating the gallbladder 14, accessing the gallbladder 14, and then treating the underlying condition that led to the need for intervention (FIG. 3). Treatments may also include, but are not limited to: providing for drainage of the gallbladder 14 and/or the biliary tree, delivering suitable materials or substances, such as antibiotics, inflammatory, anti-inflammatory agents (any of which may be short-term acting, fast acting, or time release), and/or other substances (e.g. adhesives, bioadhesives, etc.) to the gallbladder 14 and/or biliary tree, removing gallstones 20, facilitating the destruction and subsequent removal of gallstones, clearing obstructions, delivering catheters, delivering stents (drug coated or not drug coated), temporarily or permanently defunctionalizing the cystic duct 16, temporarily or permanently defunctionalizing the gallbladder 14. Devices and therapies can be delivered in a single treatment, with minimal likelihood of or necessity for follow-up or repeat procedures.

The gallbladder can be accessed by any suitable mechanism or procedure including, percutaneously, endoscopically, laparascopically, and the like. Moreover, any of the materials and substances delivered to the gallbladder can be delivered concurrently or sequentially. Delivery of substances can occur sequentially in time or the sequence of delivery can be separated by seconds, minutes, or hours.

Localization of the gallbladder 14 can be performed via endoscopic ultrasound (EUS) by accessing the wall of the GI tract with an endoscope 310 as shown in FIG. 3. Localization may also be achieved by any other method that visualizes anatomical features, such as fluoroscopy, x-rays, magnetic resonance imaging (MRI), computed axial tomography (CT) scans, ultrasound imaging from outside the body, or any method of anatomical imaging and visualization.

Once the gallbladder 14 has been located, it may be accessed and/or treated 350 through the wall of the GI tract (or any lumen in proximity to the gallbladder 14) with tools and devices (e.g. needles, guidewires, guidance catheters, dilators, etc.) delivered through, for example, an endoscope 310. Such tools and devices may be inserted down the length of the endoscope's working channel 312, or loaded onto or near the distal end of the endoscope 310. Alternately, tools and other devices may be used that do not require the aid of the endoscope for navigation or delivery. Direct visualization may be provided by the endoscope 310 during the procedure, as well as irrigation, suction, and insufflation.

Though the preferred location for accessing the gallbladder lumen is the duodenum 30, it may also be readily achieved through the wall of other regions of the GI tract, such as the stomach or the jejunum, for example. Thus, any lumen in close proximity to the gallbladder 14 is a candidate for access to and treatment of the gallbladder 14 and other members of the biliary system.

Description of the Devices:

In the present invention, in situ treatment of the gallbladder 14 is enabled via the creation of a passageway between the gallbladder lumen and a lumen in close proximity, e.g. at or near the duodenum. This passageway or duct may be created by an implantable device 420, such as those illustrated in FIG. 4.

The passageway may be temporary or permanent. It may be thought of as a fistula that is intentionally created between the gallbladder 14 and another lumen in proximity, as described above. Alternately, it may be thought of as a stoma between the gallbladder 14 and another lumen in proximity. The passageway serves as a conduit, an access port, through which a number of actions may be accomplished, drainage may be achieved, and treatments may be delivered.

A device 420 forming the passageway may be left in the patient for a short period of time, such as a few hours, a few days or a few weeks, or it may be left in place for extended periods of time, such as several weeks, months, or years. The device 420 may also be left in place permanently. If it is left in place long-term, tissue may form around the device 420, creating a fistula that connects the gallbladder 14 to the access lumen which may persist even if the passageway device 420 is removed, thus forming a biological in situ device 420 from the patient's own tissue. The fistula may be beneficial and useful, as it may continue to allow drainage for the contents of the gallbladder 14 into the small intestine. It may provide either the primary or a secondary mechanism for delivering bile into the digestive system, for example. It may also provide convenient access in cases where repeated treatments are required. Though there may be no need to close the resulting fistula, it may also be closed at any time by a clinician should this become desirable. After removal of a device 420 that initially formed the passageway, a fistula may remain open for a period of time and then close on its own, and may pose no additional risk and prove to be an acceptable course of events. Whether the device 420 is left in place or removed, and whether the fistula is left open or closed, evidence at the site may serve to mark the location of treatment in the event of future procedures.

To facilitate delivery and deployment of a device 420, it may be useful to reconfigure its shape. For example, the cross-sectional area presented by the device 420 at various locations may be reduced, thus, for example, reducing its overall profile. In cases where the configuration of the device 420 is caused to change, it may be helpful to conceive of the device 420 having one or more configurations, for example: one configuration when it is delivered (a "delivery configuration"), another configuration when it is deployed (a "deployment configuration"), and yet another configuration when it is in place and functional (a "final configuration"). Still other configurations may also be necessary or useful. For the delivery configuration, it may be advantageous to alter (e.g. reduce) the cross-sectional area or profile, so that it more easily fits delivery mechanisms, such as the working channel of an endoscope 310 (illustrated in FIG. 3). During deployment, the configuration of the device 420 may be altered so that placement into the patient is facilitated. This may be different from both the delivery configuration and the final configuration, though this is not necessarily the case. As will be appreciated by those skilled in the art, one or more configurations can be the same or substantially the same.

Figure 5A:
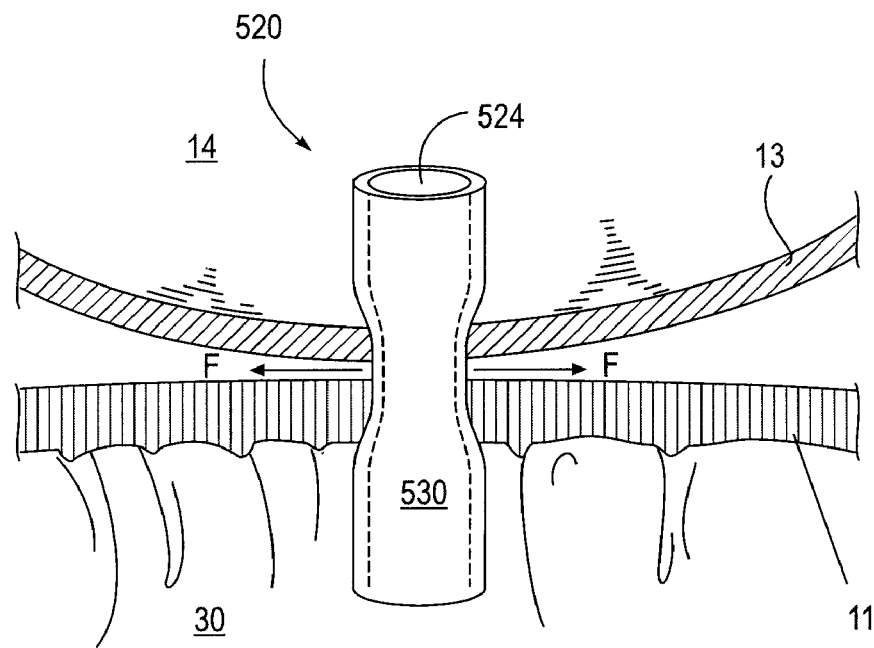
FIGS. 5A-B illustrates the outward radial force applied by an embodiment of a device adapted to provide a conduit between two body lumens.
Figure 5B:
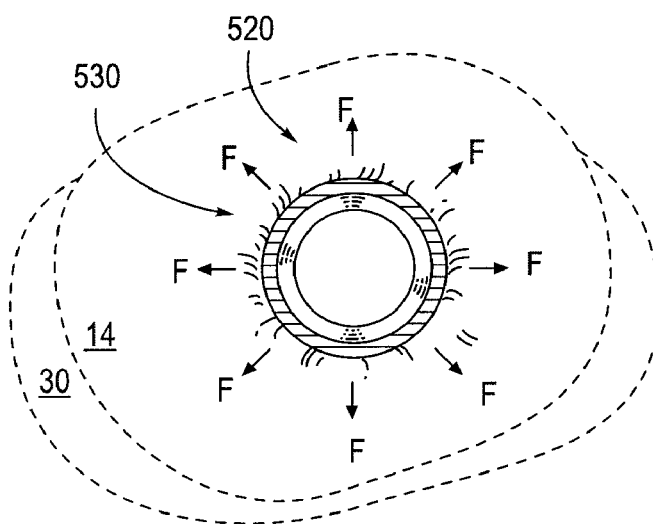

Description of the Conduit:

The preferred embodiment of the conduit is that of a short tube that is flared into hemispherical bowl-like shapes at both ends, as depicted in FIG. 4. The flared bowl-like shapes at the distal end 422 and the proximal end 425 secure the conduit device 420 in the desired location within the gallbladder 14 and the access lumen, e.g. the duodenum 30. The conduit 420 forms the proposed passageway 424 between the gallbladder 14 and the body lumen from which it will be accessed, such as through the duodenum 30. The tubular portion 430 of the conduit 420 is typically about 4-10 mm in length hl, with an inner diameter w1 of the device lumen or passageway 424 large enough to facilitate drainage and access, typically in the range of 2-10 mm. However, other dimensions can be used without departing from the scope of the invention. The outer diameter of the tubular portion 430 of the conduit 420 is typically larger than about 3 mm (10 French) in its final configuration. A variation of the preferred embodiment, depicted in FIG. 4B, comprises a short tube which is bent at an angle, rather than straight, which may beneficially accommodate anatomical variations. Another variation of the preferred embodiment, depicted in FIG. 4C, comprises a longer tube which may allow for relative motion between the gallbladder and the connected lumen, while maintaining patency of the conduit. This configuration may optionally include additional retaining features: a first 415 which is proximal to the distal retaining feature 422 and a second 419 which is distal to the proximal retaining feature 425. These additional retaining features serve to secure the tissue of the gallbladder wall and the connected lumen (e.g. the wall of the duodenum) and prevent leaks even as the structures undergo relative motion. FIG. 4D shows another variation in which the tube comprises a series of loops so that the distance h1 between the distal retaining feature 422 and the proximal retaining feature 425 may change without applying excessive force to the tissue adjacent to the anchors. As shown in FIG. 5, the tubular portion 530 may have radial compliance so that it presses gently but positively outward against the tissue it penetrates. When the original hole in the lumens' walls is smaller than the diameter of the conduit's tubular portion 530 in its final configuration, the tissue will squeeze down around the device 520 as the tube 530 generates outward radial force F. This will facilitate sealing, and prevent bile and/or other fluids from leaking into the peritoneum. The flared features 422 and 425, as illustrated in FIG. 4 serve to secure the conduit 520 in place, as well as provide slight tension to approximate the gallbladder 14 wall to the wall of the body lumen providing access. The soft and compliant nature of the preferred materials also provide for a measure of relative motion between the gallbladder 14 and connected lumen, which may increase the comfort of the patient. These retaining features 422 and 425 at either end of the device 420, as illustrated in FIG. 4, have preferred dimensions of approximately 25 mm diameter at their widest point w2, and are approximately hemispherical in shape so that their effective height h2 is approximately 12.5 mm. They may be co-molded or made as one piece together with the tubular portion 430.

Figure 6A:
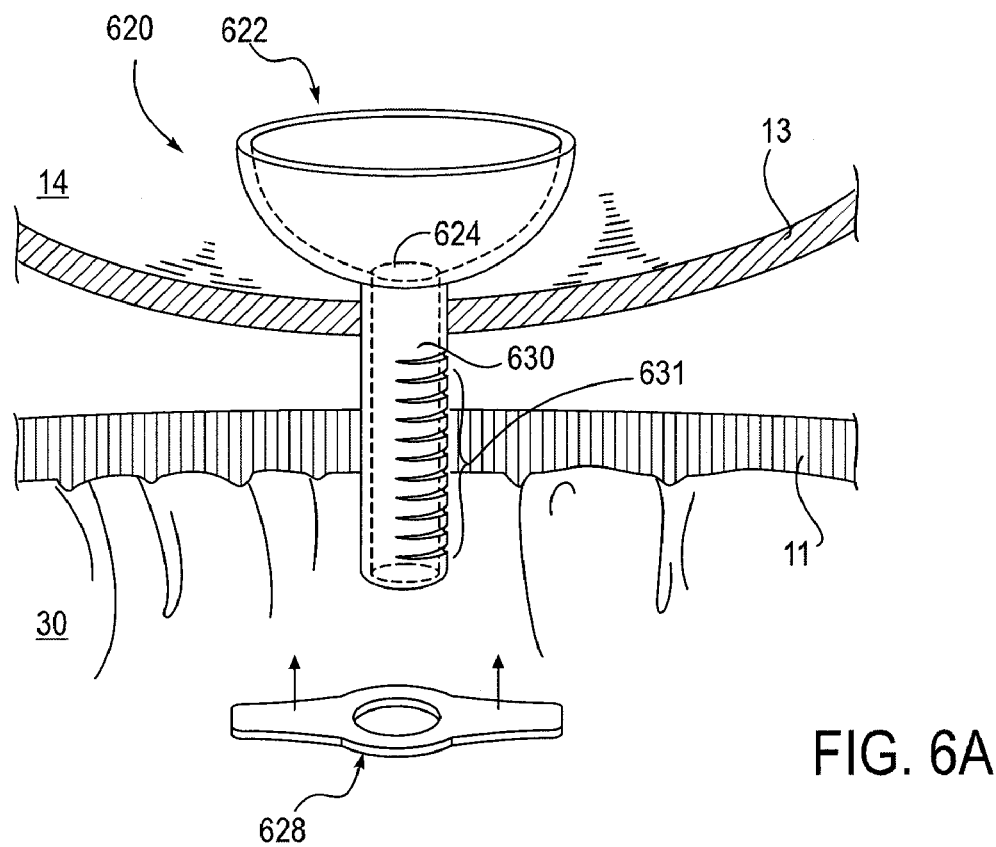
FIGS. 6A-B illustrates an embodiment of a device with a retaining feature.
Figure 6B:
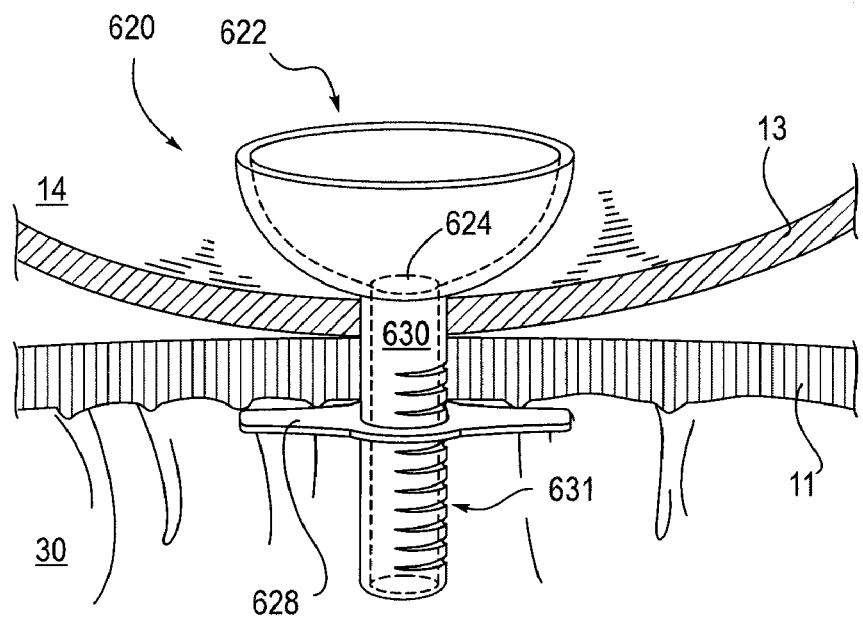

A variation on this embodiment includes an integral retaining feature 622 on one end of the device's tubular portion 630, but does not include it on the opposing end as shown in FIG. 6. In this configuration, the integral retaining feature 622 is compressed down to a minimal profile for delivery, and then allowed to expand outward during deployment. Once the device 620 is in the desired location, a retaining clip 628 may be added over the end of the tube 630 that has no integral retaining feature. The retaining clip 628 may have a single location on the tube 630 where it is securable, or it may be adjustable so that the clip 628 may be secured in a variety of locations 631. This provides for adjustability of the compression applied to the walls of the body lumens approximated by the conduit 620 (the gallbladder wall and the wall of the adjacent lumen, such as at or near the duodenum 30).

Figure 7A:
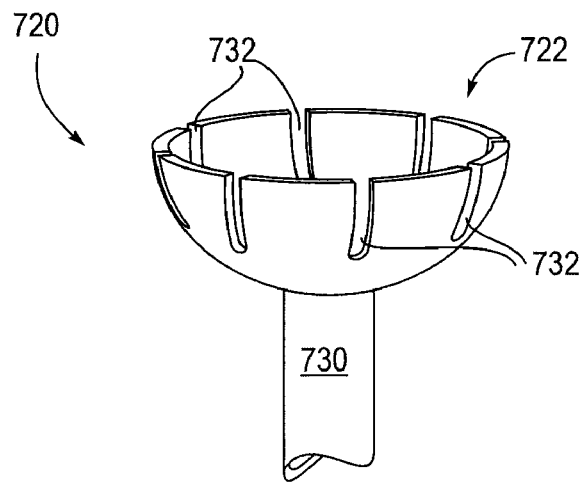
Figure 7B:
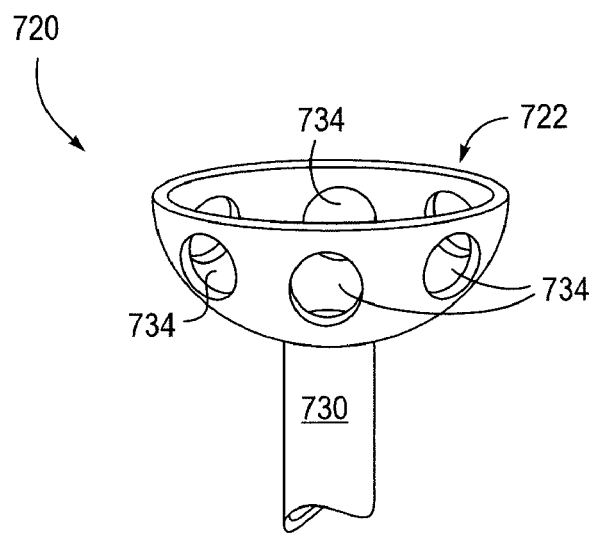

The retaining feature 422 and 425 (FIG. 4) located at either one end (as illustrated in FIG. 6) or both ends (as illustrated in FIG. 4) of the tubular portion 430 of the device 420 may be embodied in a number of different shapes. The hemispherical flared retaining feature 422 provides a measure of separation between the entry of the tubular portion 430 of the conduit 420 and the body lumen in which it resides. This may be useful in cases where it is undesirable for the contents of the body lumen to enter the conduit 420 directly (e.g. inside the duodenum 30, it may be undesirable for partially digested food to enter the conduit 420). When this bowl shaped retaining feature 422 is suspended upside down or sideways, it is especially effective at preventing ingress of undesirable matter. However, other configurations that provide less separation between the conduit 420 and the body lumen may be useful. Other designs may allow for less restricted flow of fluid from within a body lumen into the lumen of the conduit 420. This may be useful, for example, inside the gallbladder 14, where complete drainage of bile may be beneficial. An alternate embodiment based on the previously-described hemispherical shape is that of a bowl 722 with slots 732 (FIG. 7A). Another embodiment is a hemispherical shape 722 that has apertures or holes 734 incorporated into it so that it is fenestrated (FIG. 7B). The incorporation of fenestrations may be applied to any shape to allow for flow, e.g. globes, tubes, etc.

Shapes other than hemispherical bowls may also have useful properties. One such embodiment is that of a flat, or nearly flat, plate as an anchoring feature 722. This is illustrated in FIG. 7C(1). One advantage of this flat or nearly flat shape is that most or all of the fluid inside the lumen where it resides (e.g. the gallbladder 14) may pass into the conduit 720, and there will be little or no void or dead space where fluids may pool and fail to flow. The edges of a flat or nearly flat retaining feature may be rounded or curled up slightly in order to prevent trauma to adjacent tissue, FIG. 7C(2). Another variation of the shape of the anchoring or retaining feature 722 is configured so that it resembles lines of longitude of a globe, as shown in FIG. 7D. In this configuration, at least two legs 738, 738' are included (forming a complete circle), but four or more legs may be incorporated (forming two or more circles). Odd numbers of legs 738 may be incorporated, with the semicircles joined at the base 721 (the connection to the tube) and the apex 723 (the location farthest from the tube). In order to reconfigure this design to have a small cross-sectional area, which may be useful for delivery, the apex 721 may be pushed away from the tube 730, which will collapse the globe shaped retaining feature 722 into a linear configuration. This may be achieved with the use of a wire (not shown) or any other element which may push the apex 721 away from the tube 730. Another embodiment of the retaining feature 722 at the end(s) of the conduit's tubular portion resembles the shape and organization of a flower's petals 740. The petals 740 are joined at the point where they contact the tube 730 (similar to the flower's stem), and spread outwards when unconstrained, as shown in FIG. 7E. These may also be reconfigured in order to reduce the cross-sectional area, which may be useful during delivery of the device 720, and then caused to spread outwards once the device 720 is delivered and in a suitable orientation for its final configuration. Another embodiment of a device 720 has a retaining feature 722 that resembles the extensible portions of a drywall anchor or toggle, as shown in FIG. 7F. In this configuration, the retaining feature's default (unconstrained) configuration is fully extended, so that the cross-sectional area is reduced. When desired, e.g. after delivery or during deployment, the apex 723 of the extensible portions of the retaining feature may be drawn in towards the tubular portion 730 of the conduit 720, spreading out a set of legs 738 in the process. The apex 723 may be drawn in by pulling on a wire (not shown), for example, or any other element adaptable to apply tension at the apex 723. Alternately, the retaining feature's default (unconstrained) configuration may be fully contracted, so that the cross-sectional area is maximized. In this case, a wire or similar element may be used to push the apex 723 away from the tubular portion 730 of the conduit 720 to reduce the cross-sectional area for delivery.

In yet another embodiment of a device according to the invention, a retaining feature 722 has an increase in the outer diameter of the tube 730 comprising the conduit 720 (FIG. 7G). This embodiment may be configured to have a consistent outer diameter during delivery and deployment, and then configured to have an increased outer diameter for its final configuration 722, which serves to secure the conduit 720 within the body lumen.

In still another embodiment of a retaining feature 822, the device 820 is shaped in such a way that it may be pushed through a wall of a body lumen or lumens directly, and then rotated into position along with the conduit 820, to secure the two body lumens together and hold the conduit 820 in place, as illustrated in FIG. 8A. As illustrated in FIG. 8B, the retaining feature in this embodiment may be divided into more than one element 822, 822' and 825, 825', and these elements 822', 825' may be rotated radially to better secure the conduit 820 once it is in position. As shown, pairs of elements 822, 822' and 825, 825' are spread out to hold the conduit 820 in place, however any number of elements 822 and 825 greater than or equal to one could be used without departing from the scope of the invention.

As shown in FIG. 9A, a method for altering the configuration of the device 920 to facilitate delivery is to elongate the device 920. If the device 920 is sufficiently elongated, the cross-sectional area will be reduced, in some cases substantially. Once the device 920 has been elongated and its cross-sectional area reduced, it may be loaded into a sheath, capsule, or other dimensional retaining component 942 so that this low profile configuration is maintained until it is desirable to alter the configuration, such as when the device 920 is deployed or delivered in situ. Alternately, the device 920 may be compressed or elongated and then constrained by tightly wrapping or tying it with string or wire. Suitable materials for these techniques include, but are not limited to, shape memory alloys (SMA) such as Nitinol®, and cross-linked polyethylene. Another means of altering the configuration of the device 920 to facilitate delivery is to construct it so that its initial shape is that of a series of loops resembling a corkscrew, FIG. 9B. The device may be straightened and then constrained for delivery, or it may be rotated into the preferred position once the distal end has been inserted through the walls of the lumens. This configuration may incorporate at least one loop (FIG. 9C), and tissue may be retained and constrained between any two adjacent loops 922 and 931.

The conduit may be made of any suitable biocompatible material that is elastic and soft. Silicone is the preferred material. Other materials may optionally be used, e.g. polytetrafluoroethylene (PTFE), expanded PTFE, other members of the fluoropolymer family, urethanes, polyurethanes, and others. The materials can, for example, be soft at body temperature, with durometer typically in the range of 20-60 A. Softer materials are easier to deliver and reduce the risk of injury to adjacent tissue. A suitable material is, for example, soft enough to compress to a compact size for delivery and deployment.

Embodiments of retaining features 722, 822 may be comprised of compliant polymeric material (e.g. silicone). If they are comprised of soft, compliant materials, the retaining features 722, 822 can readily bend and deform to accommodate the passage of large items through the conduit 724, 824 formed between a first body lumen and a second body lumen, e.g. the gallbladder 14 and the duodenum 30. Alternately, the retaining features 722, 822 may be formed from less compliant material or a metal (e.g. Nitinol or stainless steel). The retaining features 722, 822 may be formed integrally with other elements of the overall conduit device 820, such that the components are formed to act in a unified manner by formation as a single component, or may be separate from the other elements of the overall conduit device 820. The retaining features 722, 822 may be incorporated into the overall assembly during manufacturing, or the parts may be installed by a clinician user prior to use in a patient or during deployment of the device 820 within a patient.

The device 820, or other devices described herein, may also be comprised of a biodegradable, bioabsorbable, or resorbable material, in which case it may dissolve within the mammalian body within a desirable and useful length of time. This could eliminate the need for follow-up procedures to remove the device 820 at the end of a course of treatment. Manufacturing the device 820 from such a material may not prevent clinicians from actively removing it if the need arose, however. Rather, it would prevent the need to actively remove it in cases where no other treatment was required.

Figure 10A:
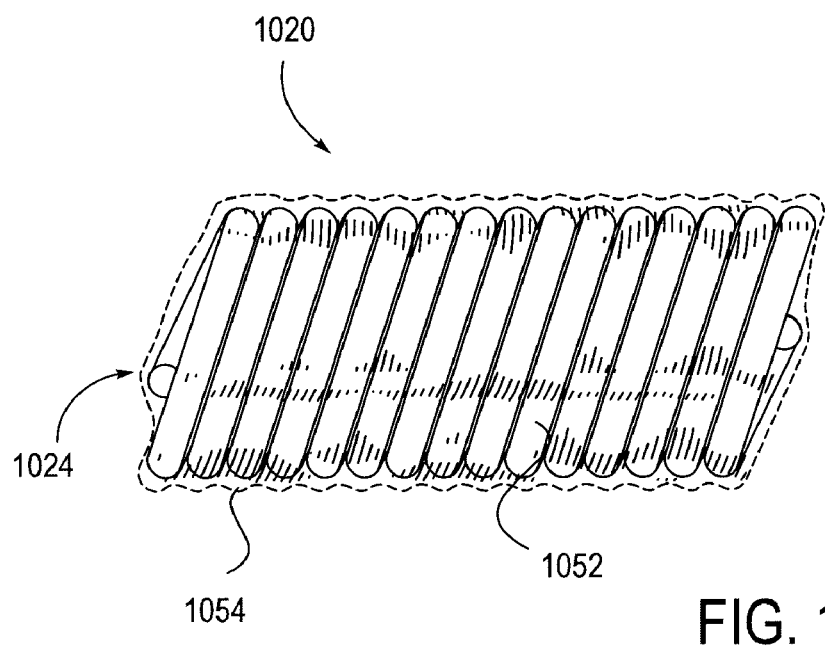
FIGS. 10A-B illustrates an alternate embodiment of a device.
Figure 10B:
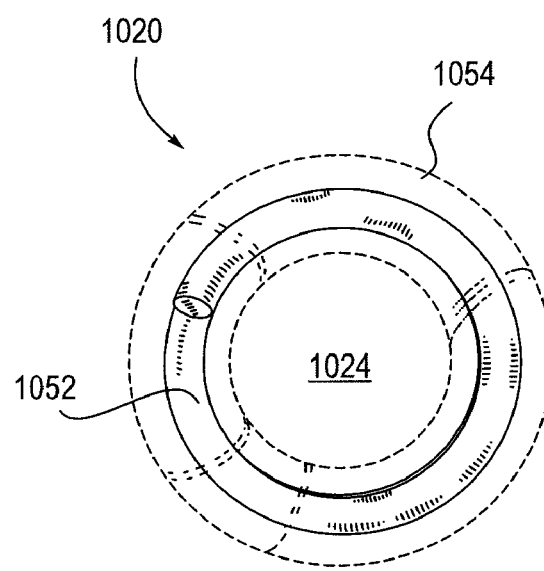

The conduit 1020 may be comprised of a single component and a single material, or it may be an assembly of different components, some of which may be of different materials that are integrally formed to act or perform in a unified manner once deployed. For instance, a conduit 1020 may be comprised of an SMA spring form 1052, over which silicone 1054 (or another suitable polymer material) is molded as illustrated in FIG. 10. The spring form 1052 serves to lend the conduit structure and dimensional stability, while the silicone (or other polymer) outer shell 1054 creates soft surfaces which are unlikely to cause injury to tissue and facilitate sealing of the device 1020 in situ and prevent leaks. If SMA materials are used, their transition temperatures can be selected to be slightly below body temperature, so that they can be designed to hold one shape for delivery and deployment, and, after transitioning, they will have the desired shape(s) for optimizing the function of the conduit. Alternately, the SMA material may be used in its superelastic state.

Figure 11:
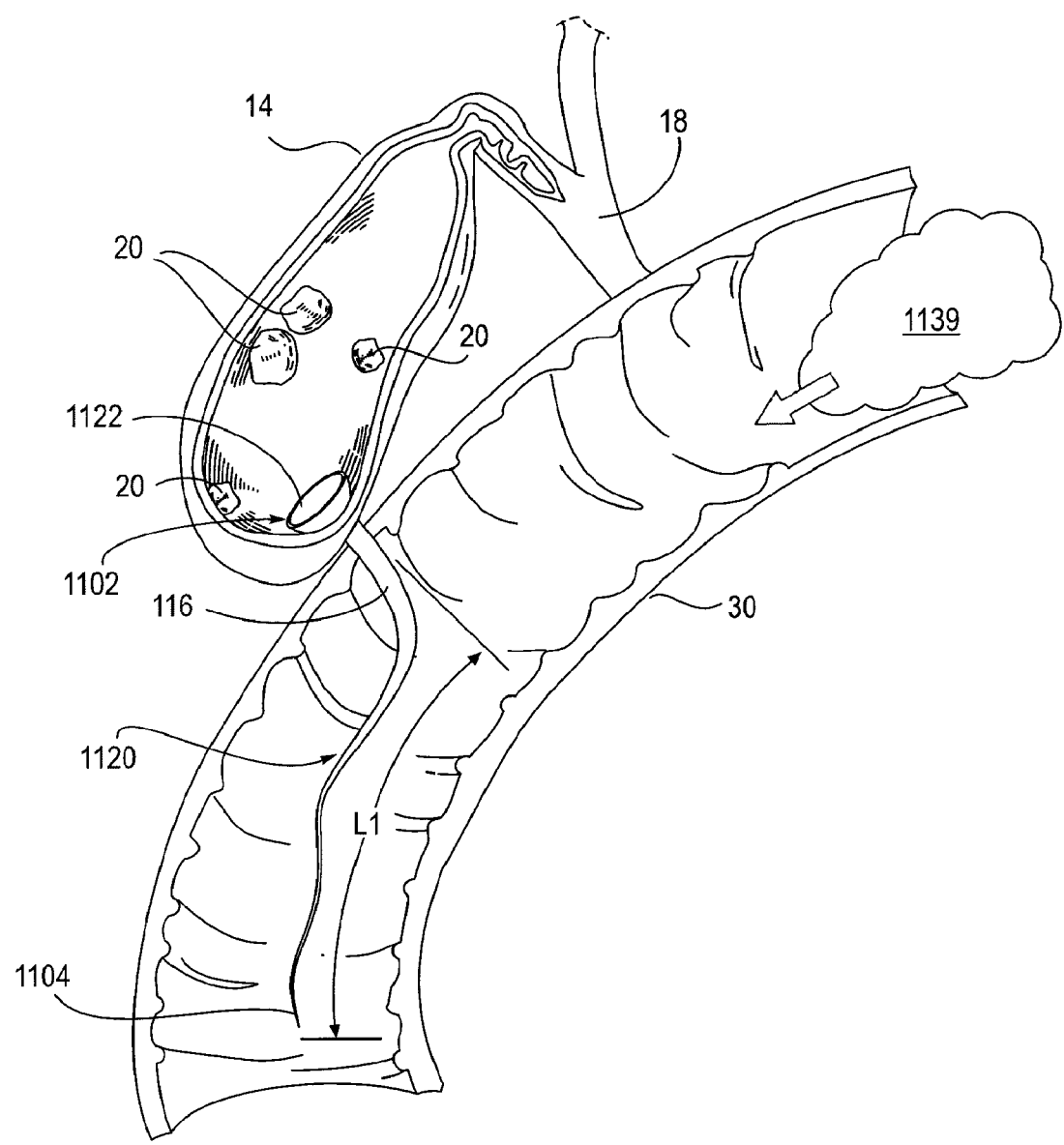
FIG. 11 illustrates an alternate embodiment of a device having an elongate tube.

As shown in FIG. 11, an alternate embodiment of the conduit device 1120 is formed from an elongate tube 1130 which incorporates a retaining feature 1122 to secure a distal end 1102 (the end within the lumen of the gallbladder 14), a distal end 1102 with sufficient structure to maintain the conduit tube's 1130 patency, a proximal end 1104 that may lack sufficient structure to maintain the conduit tube's patency, and/or an overall length L1 sufficient to deliver bile from the gallbladder 14 into the duodenum 30 a length downstream of the location that the duodenum 30 and the gallbladder 14 are connected by the conduit 1120. If the conduit 1120 is configured so that patency of the proximal end 1104 is not maintained, the tube 1130 may be thought of as highly flexible so that it may be easily moved and/or deformed by materials such as chyme 1139 moving through the small intestine. Downstream delivery of bile into the duodenum 30 may be desirable to prevent bile reflux, a condition that occurs when bile enters the patient's stomach and/or esophagus. For such an embodiment, the length of the tube 1130 may be adjustable. For example, the conduit may be placed into the gallbladder 14 and then trimmed to the desired length. Alternatively, the conduit 1120 may be made available to clinicians in a variety of lengths.

Another alternate embodiment of the conduit device 1220 as illustrated in FIG. 12A, is comprised entirely of SMA, such as Nitinol. In this embodiment, the radial dimensions of the conduit's tubular portion 1230 may be reducible to facilitate delivery. Methods of achieving this include, but are not limited to: cutting the tube wall parallel to its central axis x and rolling the material tightly to reduce the diameter d for delivery, then expanding it to a greater diameter D and rejoining the edges to form a complete and sealed tubular structure at deployment; simply folding or radially collapsing the tube 1230 to a smaller outer diameter dl which may be the minimum possible radial dimension from which the SMA material can fully recover its desired tubular diameter d2 and shape at deployment (FIG. 12B); forming the tube 1230 into a polygon which, in its collapsed configuration folds in an "asterisk" pattern to present minimal cross-sectional area with diameter d1, and in its expanded configuration is a polygon approximating a circular cross-section with diameter d2 (FIG. 12C). For the configuration depicted in FIG. 12C, the number of sides of the polygon can vary, with higher numbers of sides resulting in beneficial characteristics such as the device 1220 more closely approximating a circular cross-section when expanded and collapsing to smaller sizes to facilitate delivery and deployment.

Figure 13F:
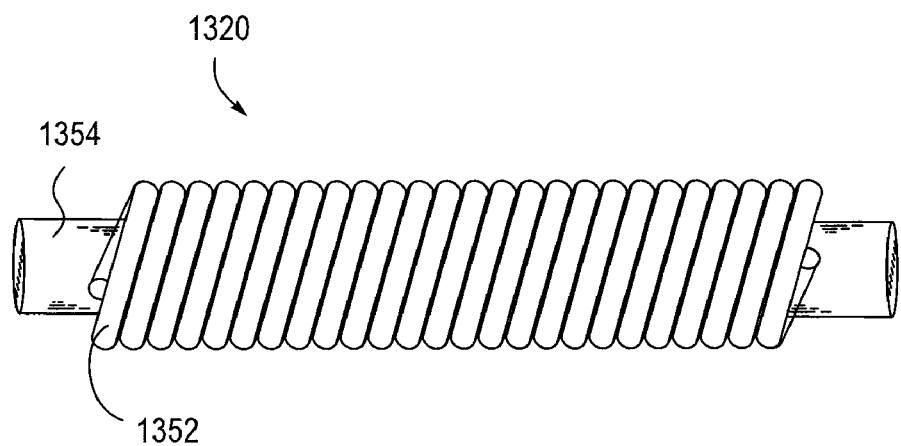
Figure 13G:
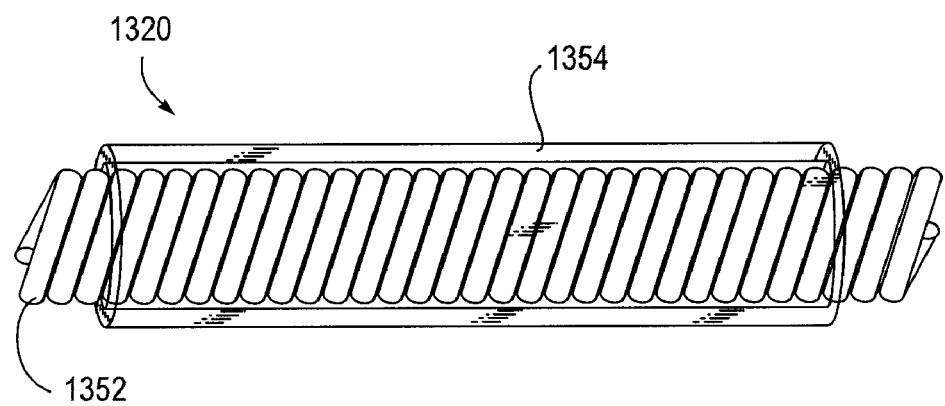

Turning now to FIG. 13, an alternate embodiment is depicted that may be comprised entirely of SMA or other material is that of a close-wound spring. The spring 1352 may be formed by tightly coiling a wire-shaped material, such as Nitinol, other SMA material, stainless steel, titanium, or other suitable material so that it forms a coil as shown in FIG. 13A. This coil 1352 shares characteristics with an extension spring: if tension is applied at the ends of the component, the coils are caused to separate, and this results in the spring creating a compressive return force F. When no external tension is applied to the coil, the gaps between the individual winds of the coil are minimal, and these gaps may be maintained by residual compressive forces imparted to the material during manufacturing as shown in FIG. 13B. To configure such an embodiment for delivery, a tensile load F may be applied, and/or the proximal and distal ends of the spring may be rotated relative to each other T, greatly increasing the length of the device 1320, decreasing the cross-sectional area and diameter d accordingly as shown in FIG. 13C. Once the device 1320 is in the desired configuration for delivery, it may be loaded into a sheath or other retaining component as shown in FIG. 13D so the configuration is maintained until it is desirable to alter the configuration, such as when the device 1320 is deployed. A variation of this embodiment includes a coating 1354 of the material comprising the spring 1352 with a soft, easily deformable polymeric material, such as (but not limited to) silicone, PTFE, or EPTFE as illustrated in FIG. 13E. This could also be achieved by overmolding the polymeric material onto the spring. This coated spring device 1320 has the characteristics described above, as well as the advantages of a soft, compliant, sealed surface: e.g. the potential for bile leaks is reduced (as well as other fluids), and a reduction of the likelihood of injury to surrounding tissue by the device 1320 or the acts of delivering and deploying the device 1320. Alternately, the spring 1352 could be located outside the soft, compliant material 1354, as illustrated in FIG. 13F, or inside, as illustrated in FIG. 13G.

Figure 14A:
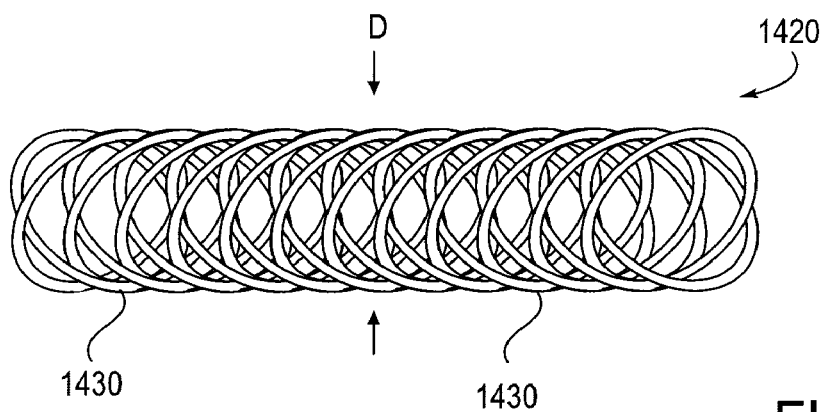
FIGS. 14A-B illustrates a stent-like embodiment.
Figure 14B:
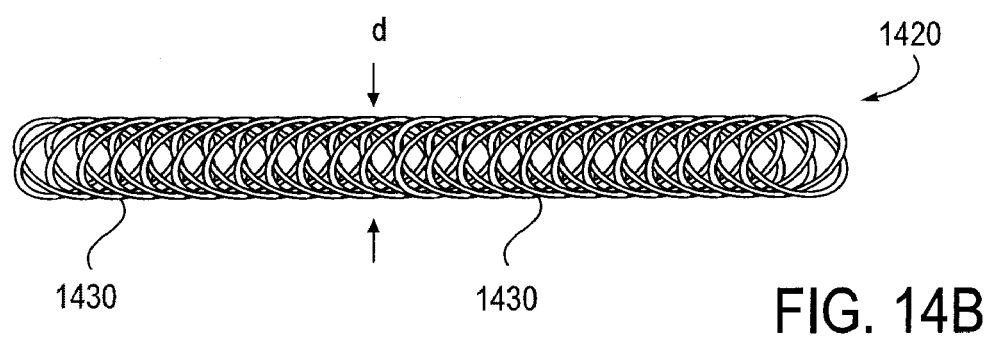

In another embodiment, the structure of the conduit's tubular portion 1430 may be comprised of SMA (such as Nitinol or other suitable material) or non-SMA material (e.g. stainless steel or polymeric material) in the form of a stent as shown in FIG. 14. The stent 1420 may be covered or may cover another material (such as silicone or EPTFE, as described above) so that it provides a sealed passageway between the gallbladder 14 and the connected body lumen. During delivery, the stent 1420 presents a very small cross-sectional area with initial outer diameter d. During deployment, the stent 1420 is caused to expand outwards against the hole in the walls of the body lumens it connects together. This outwards, radial force of the device 1420 and increase in outer diameter D may be optimized in such a way as to reduce the risk of leaks between the gallbladder 14, the connected body lumen, and the surrounding anatomy.

Leaks may also be prevented by coating the external surfaces of any conduit design with a suitable adhesive, such as one that is biocompatible. Such an adhesive serves to bond the device 1420 to the tissue it contacts, and prevents gaps which may otherwise allow fluid to escape from either lumen or the conduit itself.

The conduit's retaining features 1522 located at either end may also be comprised of SMA (e.g. Nitinol) or other suitable non-polymeric material. This may be the case whether the tubular portion 1530 of the conduit 1520 is formed from the same or from different materials. Such retaining features may take on a number of shapes and configurations. FIG. 15A shows one embodiment in which the retaining features 1522 resemble spring form fingers 1558, spread out in a flared pattern from the ends of the conduit's tubular portion. During delivery, the fingers 1558 are compressed in towards the central axis x of the tube 1530 to reduce the profile. Upon deployment, the fingers 1558 are allowed to spread outwards to function as a retaining feature 1522. FIG. 15B and FIG. 15C show other embodiments in which the retaining feature 1522 comprises an element 1558 in a spiral configuration that resembles a corkscrew, with a variable outer diameter. During delivery, this spiral is compressed to reduce its profile, and upon delivery it is caused to expand outwards to serve the purpose of retention.

Figure 16A:
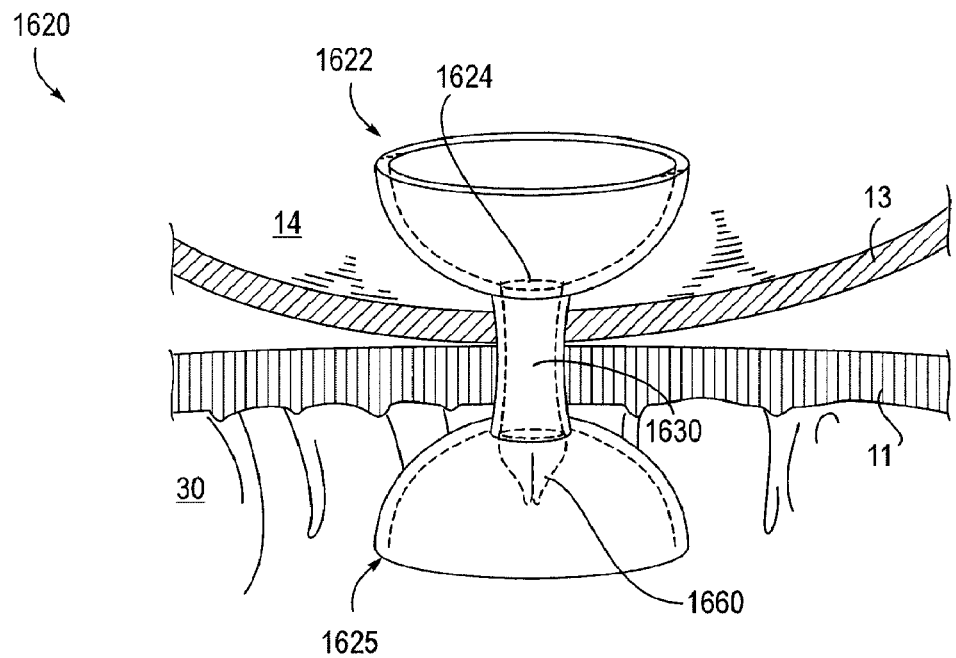
Figure 16B:
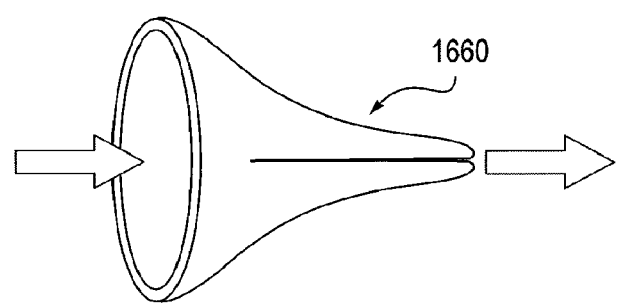
Figure 16C:
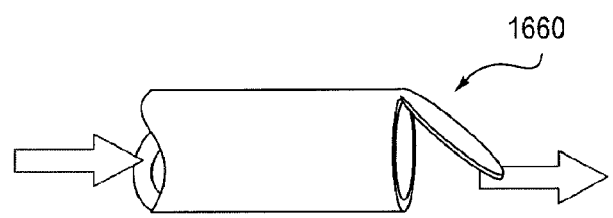

To ensure that material is only allowed to travel through the conduit from the gallbladder 14 into the lumen connected via the conduit, e.g., the duodenum, and not in the reverse direction, a valve 1660 may be incorporated into or attach onto the conduit device 1620. For instance, it may be desirable to deliver bile into the digestive tract, and to drain pus or other fluids, but undesirable for partially digested food to move from the small intestine into the gallbladder 14. A valve may be used to prevent flow into the gallbladder 14 from sources other than the biliary system. This is illustrated in FIG. 16. Among the purposes of the valve 1660: allow the movement of material from the gallbladder 14 into the body lumen (e.g. a duodenum 30) connected by the conduit 1620, prevent flow in the reverse direction, and control the level of pressure that is allowed to develop within the gallbladder 14. Controlling the pressure within the gallbladder 14, and ensuring that the pressure differential between the gallbladder 14 and the connected body lumen remains low, reduces the risk of the bladder's contents (e.g. bile) leaking into the peritoneum. Bile leaks can result in bile peritonitis. The valve 1660 may be incorporated or added at any location within the conduit, from the most distal end (the farthest end inside the gallbladder 14) to the most proximal end (the closest end inside the connected lumen), as shown in FIG. 16A. The valve may be made of any suitable material, such as the materials used to construct the conduit. The preferred material for this purpose is silicone. However, it may also be made of any other suitably biocompatible compliant material (in cases where bending characteristics of the material are used to create the flow control feature) or non-compliant material such as stainless steel, nickel-titanium alloy, or titanium (in cases where mechanical elements are used to create the flow control feature). The preferred embodiment is that of a duckbill valve illustrated in FIG. 16B, with a slit in a cone-shaped compliant material that supplies elastic forces that cause it to be closed under normal circumstances, open when the pressure in the gallbladder 14 exceeds the pressure in the connected lumen (e.g. during contraction of the gallbladder 14) by a desired amount, and closed if the pressure in the connected lumen is higher than the pressure in the gallbladder 14 (a condition that might otherwise result in flow in the undesirable direction). In an alternate embodiment, the valve may be designed as a sprung flap (FIG. 16C), with functional characteristics similar to those of the duckbill valve described above. Another embodiment is that of a bicuspid valve (FIG. 16D) or tricuspid valve (FIG. 16E), which also exhibit the characteristics of allowing flow from the gallbladder 14 into the connected body lumen, but not in the reverse direction. Each of these embodiments, and other valve embodiments not specifically described herein, share the flow control characteristics of a) allowing flow from the gallbladder 14 into the body lumen connected through the conduit 1620 when the pressure in the gallbladder 14 is greater than the pressure in the connected lumen by a desired amount, b) not allowing flow from the connected lumen into the gallbladder 14 when the pressure in the lumen exceeds the pressure in the gallbladder 14, and c) not allowing flow between the gallbladder 14 and the connected lumen when little or no pressure differential exists between the two bodies.

An adjustable valve 1660 may also be incorporated into or added to a conduit 1620. Such a valve would enable practitioners or patients to adjust the difference in pressure between the gallbladder 14 and the connected lumen (such as the duodenum) at which the valve opens. Adjustability may be incorporated into the valve body in such a way that a clinician may adjust it endoscopically, or it may be incorporated in such a way that a clinician or the patient may adjust the valve without requiring additional endoscopy or invasive procedure.

Another approach to controlling flow between the gallbladder 14 and a connected body lumen is to incorporate or allow for the installation of a blocking mechanism or plug to close off the conduit. This may be in addition to, instead of, or interchangeable with a valve 1660, as described above. The plug may allow for temporary or permanent blockage of the passageway between the gallbladder 14 and the connected body lumen created by the conduit. One embodiment of such a plug is as a diaphragm 1770 or membrane (FIG. 17A) that allows for short term access to the gallbladder 14 through the conduit by puncturing the material at the center of the block. This may be accomplished, for example, with a needle or fine catheter. The material of the diaphragm or membrane may be selected so that it is self-healing, and as such is re-sealable. This may allow for multiple instances of puncture and hence able to be used for repeated access. Another embodiment of such a plug 1770 is that it is installable, removable and/or replaceable (FIG. 17B). These functions may be performed endoscopically.

Delivery of Materials or Substances to the Gallbladder

In some aspects it may be desirable to deliver one or more materials, such as fluids or gases, to the interior of the gallbladder lumen either before or after delivery of any of the devices disclosed herein. Moreover, any of the materials and substances delivered to the gallbladder can be delivered concurrently or sequentially. Delivery of substances can occur sequentially in time or the sequence of delivery can be separated by seconds, minutes, or hours.

An amount of fluid, gas, or material delivered as described throughout can be such that it fills the gallbladder, substantially fills the gallbladder (e.g., fills more than 50% of the gallbladder, more than 75% of the gallbladder, more than 85% of the gallbladder, more than 90% of the gallbladder, more than 95% of the gallbladder, or more than 99% of the gallbladder) or is activatable to fill or substantially fill the gallbladder. Alternatively, in some instances, e.g., the amount of fluid, gas, or material delivered as described throughout can be such that it coats the interior lumen of the gallbladder, or substantially coats the interior lumen of the gallbladder (e.g., coats more than 50% of the gallbladder, more than 75% of the gallbladder, more than 85% of the gallbladder, more than 90% of the gallbladder, more than 95% of the gallbladder, or more than 99% of the gallbladder).

Description of the Delivery Mechanisms:

Delivery of the conduit may be accomplished in a variety of ways. An examplar delivery method is shown in FIG. 18, and a flowchart illustrating the method is shown in FIG. 19. The examplar delivery method shown in FIG. 18A involves using an endoscope 1810 to place one or more guidance elements 1880 (for example a needle, a guidewire, and/or a guidance catheter) between the access body lumen (e.g. the duodenum, stomach, or jejunum) and the gallbladder 14. In cases where a needle, a guidewire and/or a guidance catheter are used, a guidance catheter may be advanced in the patient's gastrointestinal tract, often but not necessarily within the working channel 1812 of an endoscope 1810, until the distal tip of the guiding catheter is proximal to the desired placement location for the device 1820. A needle may be advanced out of the distal end of the guiding catheter through the wall in the gastrointestinal tract, e.g. at a duodenum 30, continuing through the wall of the gallbladder 14, and into the lumen of the gallbladder 14. As an optional step, bile may be aspirated through the needle or any other guidance element 1880 to reduce the pressure within the gallbladder 14, reducing the risk of bile escaping the gallbladder within the peritoneum. To facilitate this, the guidance element (e.g. needle, guidewire, guidance catheter) may incorporate an aspiration port, either distal or anywhere along a surface or wall. As another optional step, a guidewire may be inserted into the gallbladder lumen through the needle. In cases where a guidewire is used, the needle may be withdrawn once the guidewire has been inserted. When desirable, either the guidance catheter or a separate dilatation catheter, having an inflatable balloon 1885 on the distal portion thereof, may be advanced over the previously introduced needle or guidewire until the balloon 1885 is properly positioned through the wall of the gastrointestinal tract and the wall of the gallbladder 14. Once in the desired position, the dilatation balloon 1885 may be inflated with inflation fluid one or more times to a predetermined size so that the tissue around the puncture site is expanded to accommodate the device 1820. Generally, the inflated diameter of the section of the balloon contacting the wall of the gallbladder 14 and gastrointestinal tract access lumen is slightly smaller than the outer diameter of the tubular portion 1830 of the device 1820 that will be inserted through the puncture. In one approach, the device 1820 may then be guided into position over the guidance element(s) 1880 (e.g. needle, guidewire, guidance catheter) through the hole in the wall of the gastrointestinal tract and the wall of the gallbladder 14 to the desired depth. Once in the desired position, the device 1820 may be deployed and held in position by its retaining features 1822 and the adjacent tissue.

Figure 18A:
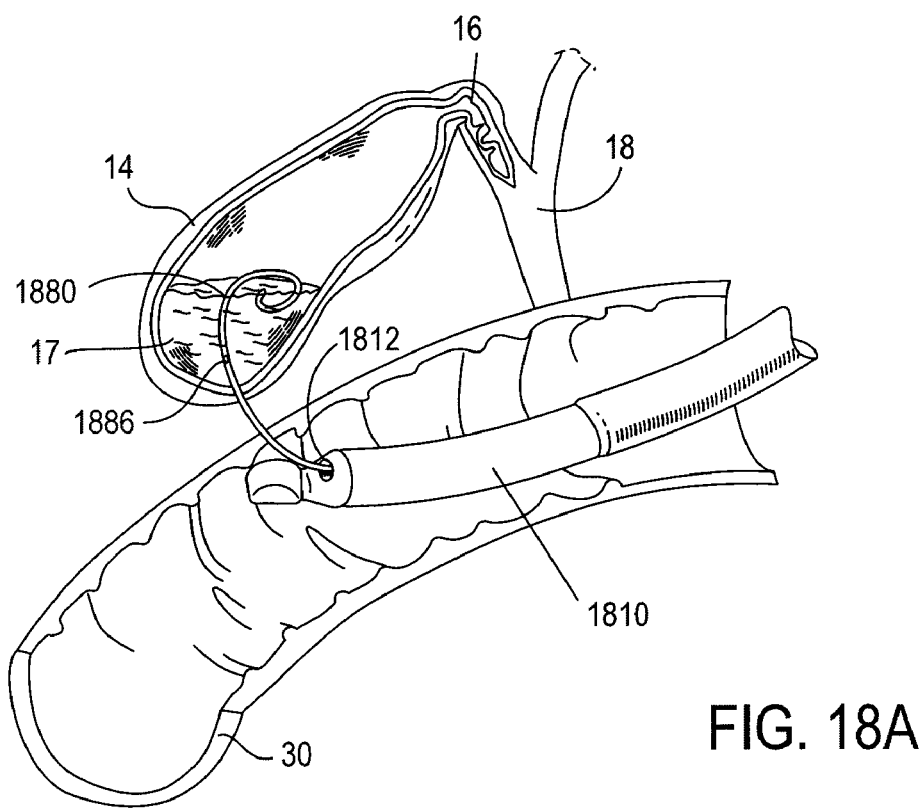
FIGS. 18A-I illustrate delivery of a device according to the invention via a catheter.
Figure 18B:
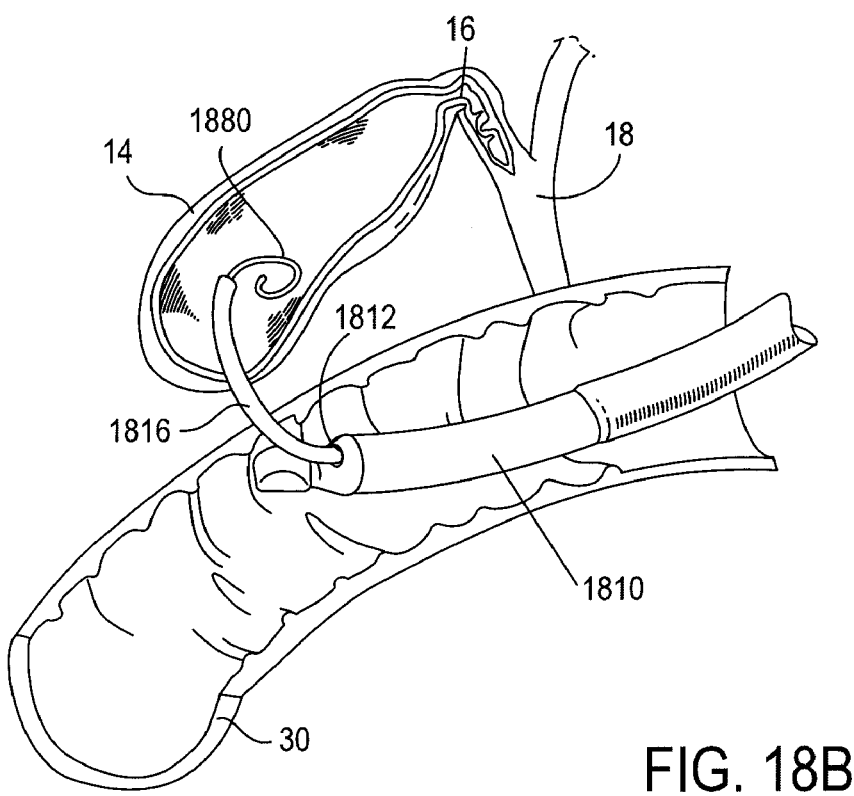
Figure 18C:
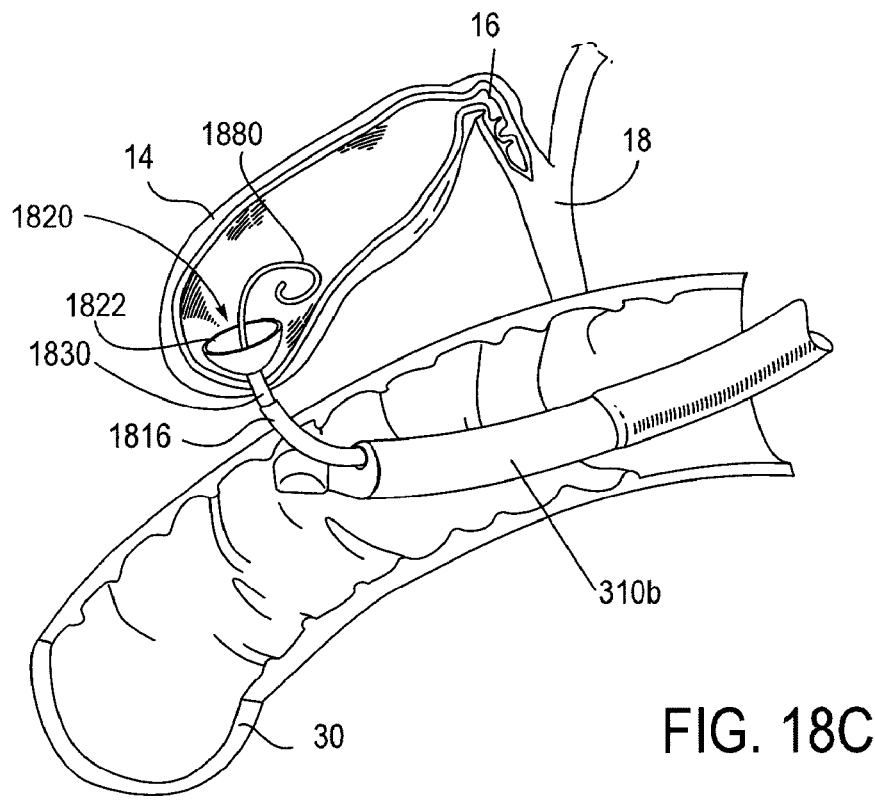
Figure 18D:
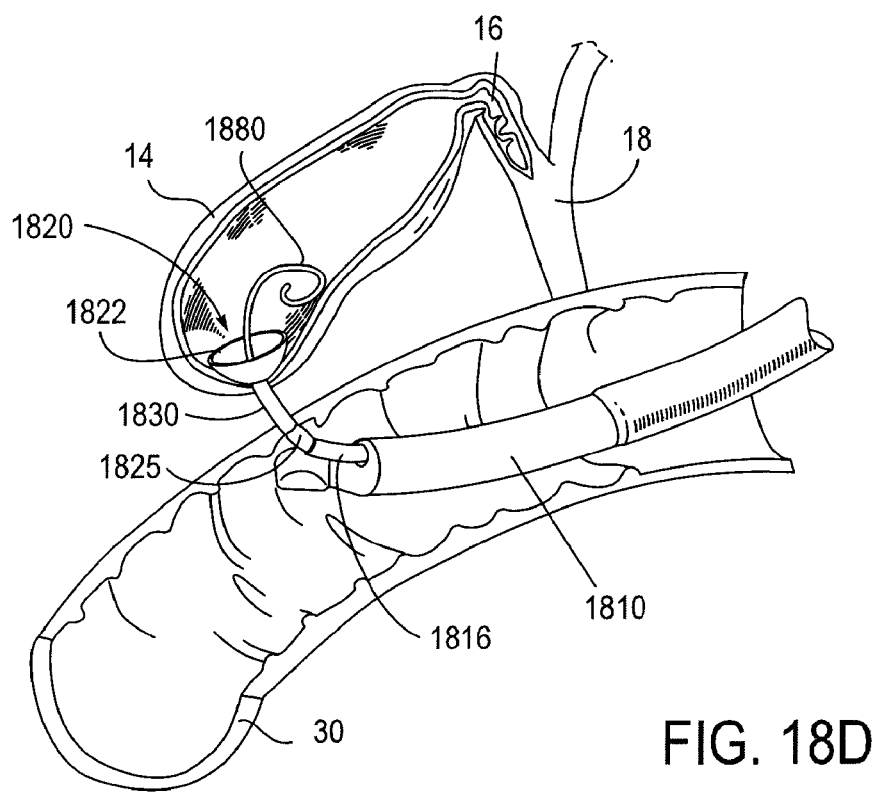
Figure 18E:
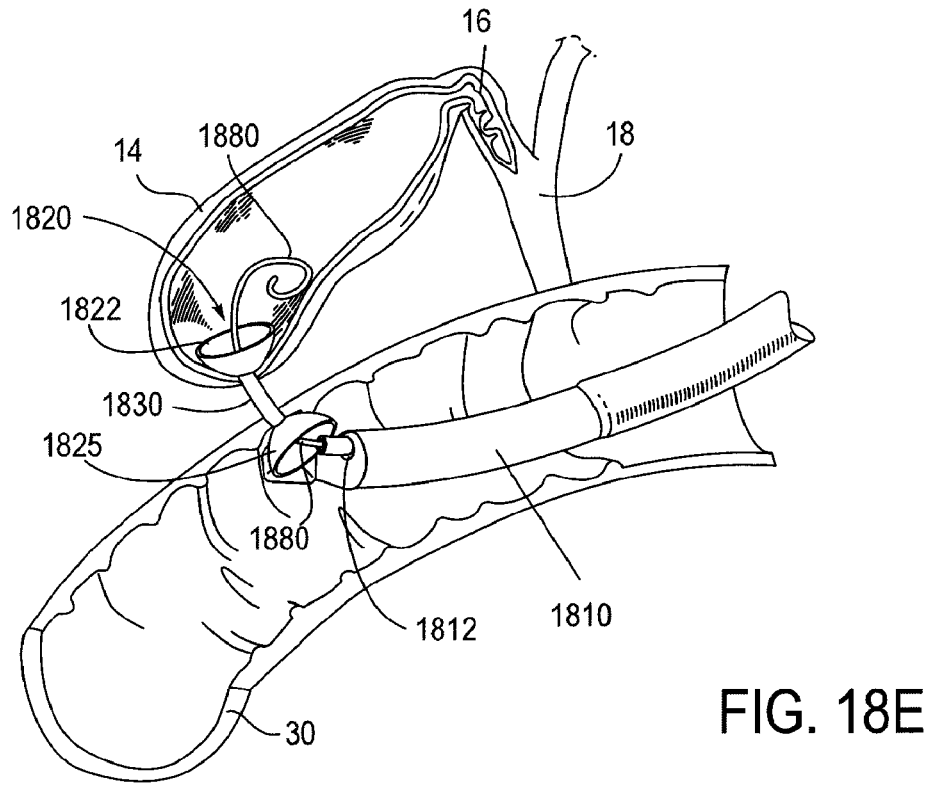
Figure 18F:
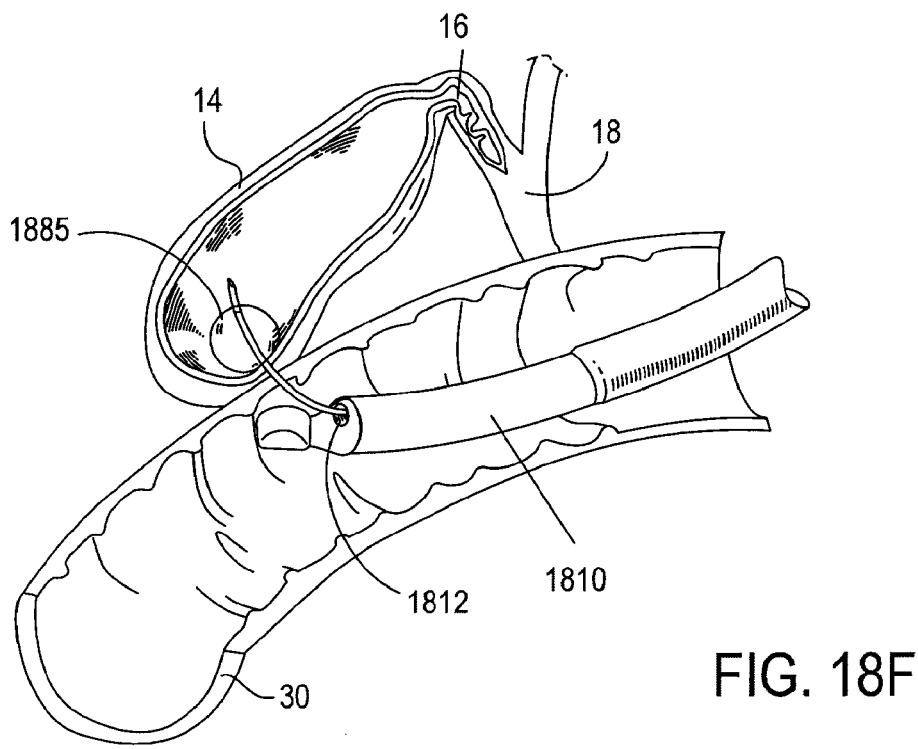
Figure 18G:
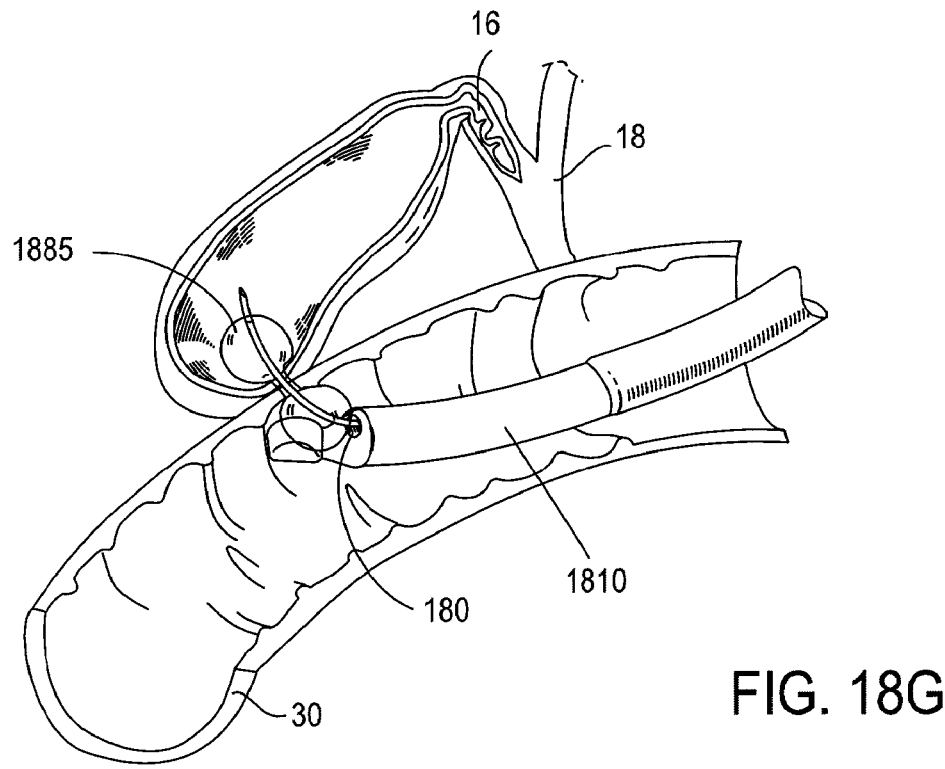
Figure 18H:
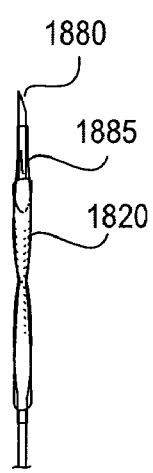
Figure 18I:
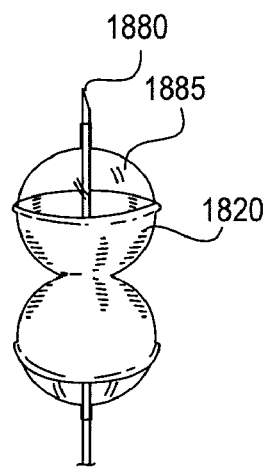
Figure 19:
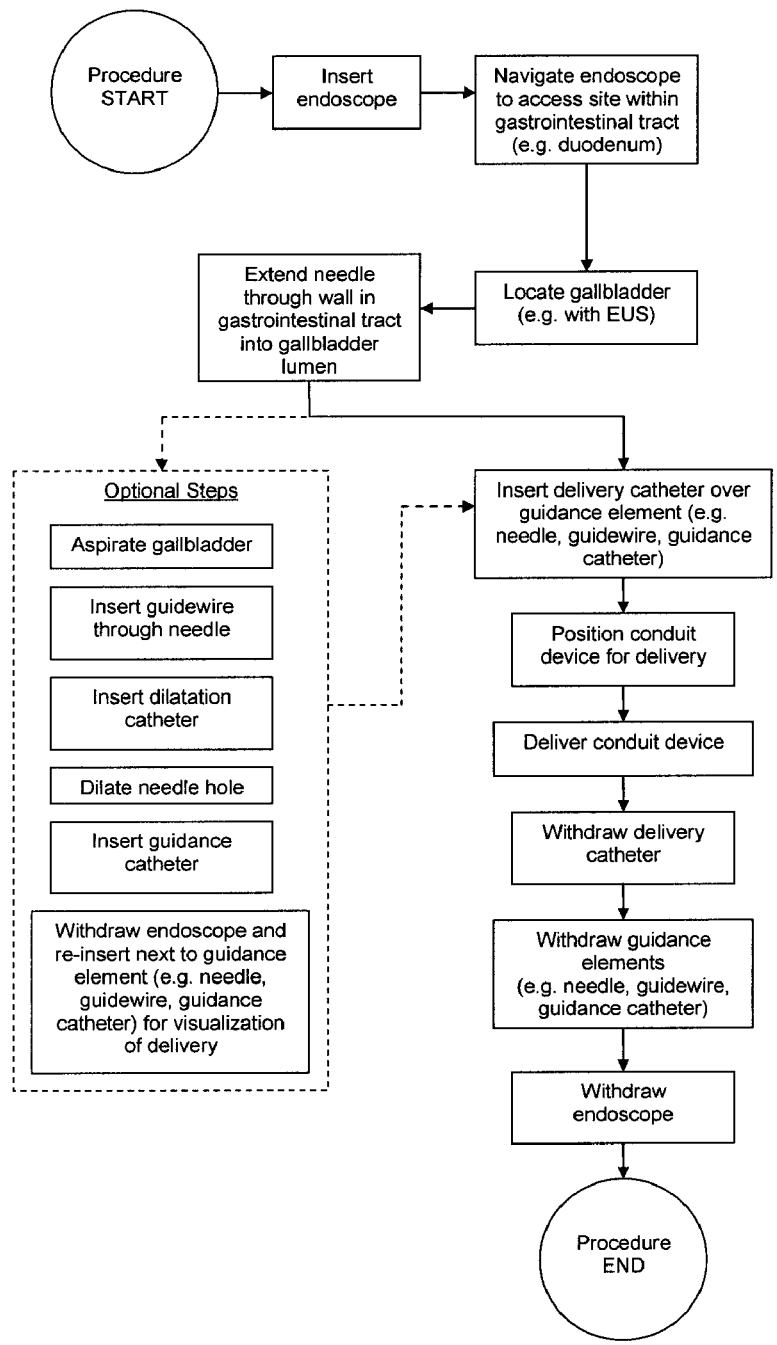
FIG. 19 illustrates the steps of delivering a device according to the invention via a catheter.

When the device 1820 is delivered in conjunction with a guidance element 1880 such as a needle, a guidewire, and/or a guidance catheter, the device 1820 may be positioned within a delivery catheter 1816 that constrains the device 1820 in its delivery configuration (FIG. 18B). The delivery catheter 1816 may incorporate a separate lumen to accommodate the guidance element 1880. When the device 1820 is placed in the desired position, the delivery catheter 1816 may be manipulated or repositioned relative to the device 1820 in order to deploy the device 1820 and effect its reconfiguration into the deployed configuration or the final configuration (FIGS. 18C-E). Manipulation of the delivery catheter 1816 may, for example, include activation of a deployment device such as a balloon section 1885 (FIG. 18F). The balloon profile may have a consistent profile, or it may have a varied profile, such as that shown in FIG. 18G. A varied balloon 1885 profile may facilitate tissue approximation (e.g. the wall of the gallbladder 14 and the wall of the gastrointestinal tract access lumen such as a duodenum 30) during dilatation and delivery steps. As described above, it may be desirable for the pilot hole for the guide element 1880 to have a small diameter relative to the size of the conduit device 1820 to be installed, in order to create a better seal between the surfaces and reduce the risk of leaks. Once the guidance element 1880 (e.g. a guidewire) is in place, a delivery catheter 1816 may be inserted over the guidance element 1880 and into the gallbladder 14. The delivery catheter 1816 carries the conduit device 1820 and conduit deployment device, such as a balloon section 1885, which can be expanded to both dilate the tissue and deploy the conduit 1820 into a deployed or final configuration once it is positioned in the desired location (FIG. 18G-I). Once the conduit 1820 has been deployed, the delivery catheter 1816 and any other delivery elements 1880 (e.g. needle, guidewire, etc.) may then be withdrawn, leaving the conduit 1820 in place. The delivery catheter 1816 may be sized to fit in the working channel 1812 of a typical endoscope 1810. When resident on or in the delivery catheter 1816 prior to deployment, the conduit device's 1820 outer profile may be similar to that of the delivery catheter 1816, facilitating insertion and reducing the potential to catch or snag anywhere during delivery. When the conduit 1820 has been placed properly and connects the gallbladder 14 and the access body lumen, the conduit 1820 may be deployed and secured in place.

Figure 20:
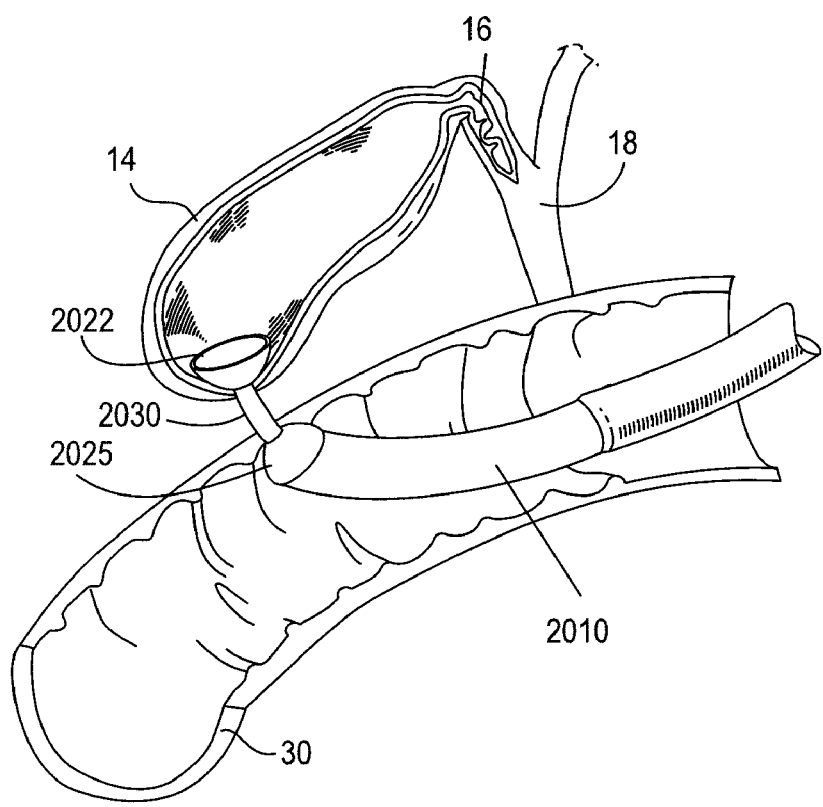
FIG. 20 illustrates delivery of a device according to the invention at the distal tip of an endoscope.

Another delivery method is to mount either the conduit 2020 or a holder for the conduit on the distal end of an endoscope 2010. After navigating to the desired location with the endoscope 2010, the conduit 2020 may then be inserted through the wall of the access body lumen and the gallbladder 14 to form the desired passageway. This is illustrated in FIG. 20.

For delivery methods that involve the use of a guidewire, the guidewire could be of a traditional design and used according to conventional methods. In this case, a length of guidewire is inserted into the gallbladder 14 through the wall of the gallbladder. An extra length of guidewire is then inserted and allowed to accumulate within the gallbladder 14, thus passively retaining the guidewire distal end in the gallbladder 14 while the guidewire is used to deliver additional elements. This type of guidewire has no additional feature that serves to retain the distal end within the gallbladder 14 during treatment: the distal end floats freely in the lumen of the gallbladder 14, and withdrawal involves simply pulling the guidewire from the proximal end.

Figure 21A:
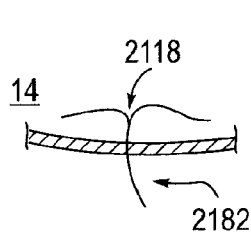
FIGS. 21A-H illustrate a guidewire retention feature.
Figure 21B:
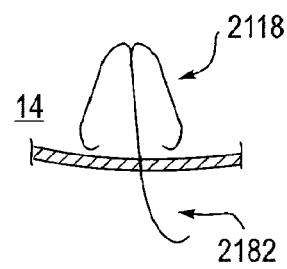
Figure 21C:
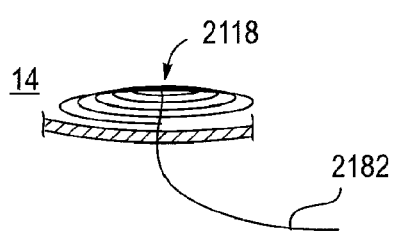
Figure 21D:
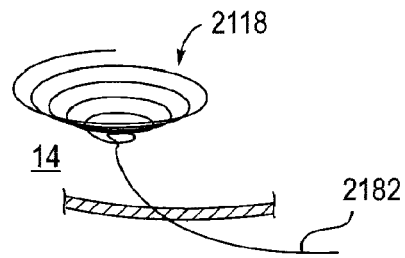
Figure 21E:
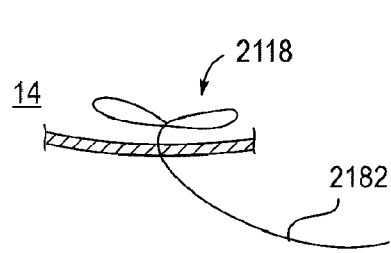
Figure 21F:
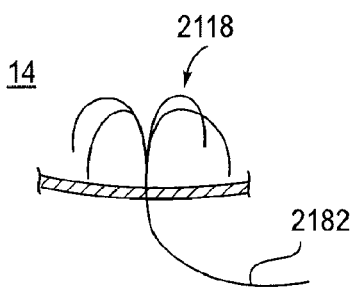
Figure 21G:
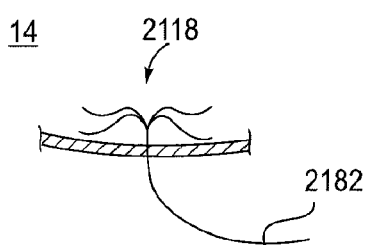
Figure 21H:
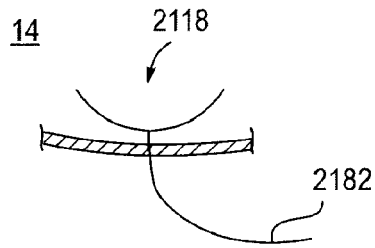

An alternate embodiment of the guidewire 2182 includes a retention feature 2118 to retain the distal end once it has been successfully inserted into the gallbladder 14 lumen. This allows for the guidewire 2182 to be placed under increased tension without the risk of pulling it out of the gallbladder 14 unintentionally. The ability to place the guidewire 2182 under tension may be useful, for instance, when approximating the walls of the access body lumen and the gallbladder 14, during the insertion of a delivery catheter (not shown), and delivery and/or deployment of a conduit. The feature 2118 on the distal end of a guidewire 2182 that provides for retention may have a number of different shapes, such as a "T" (FIG. 21A), an arrow head (FIG. 21B), a flat spiral (FIG. 21C), a funnel-shaped spiral (FIG. 21D), a folding compliant tag (FIG. 21E), a grappling hook (FIG. 21F), spreading wings (FIG. 21G), or a whale's tail (FIG. 21H). A retention feature may be engaged by first inserting the guidewire 2114 into the gallbladder lumen, then pulling back on the guidewire 2114 until the retention feature engages with the gallbladder wall. The guidewire is typically made of Nitinol, however it may be comprised of any material that is capable of elastically bending with the required radii and supporting the required tension in a thin, small profile.

Kits:

All of the devices required to deliver and install a conduit may be packaged in a kit. Bundling all devices, tools, components, materials, and accessories needed to perform these procedures into a kit may enhance the usability and convenience of the devices, and also improve the safety of the procedure by encouraging clinicians to use the items believed to result in the best outcomes. The kit may be single-use or reusable, or it may incorporate some disposable single-use elements and some reusable elements. The kit may contain, but is not limited to, the following: implantable and/or non-implantable devices; delivery devices (e.g. needles, guidewires, guidance catheters, dilators, etc.); balloon inflation/deflation accessories; syringes; fluid flow, temperature, and pressure measurement instruments; scissors; scalpels; clips; ablation catheters; endoscopic tools (e.g. lithotripsy devices, snares, graspers, clamps, forceps, etc.). The kit may be supplied in a tray, which organizes and retains all items so that they can be quickly identified and used.

Description of Other Uses:

The techniques and devices described in this application may prove beneficial in applications beyond their initial use in the treatment of biliary disease.

Figure 1:
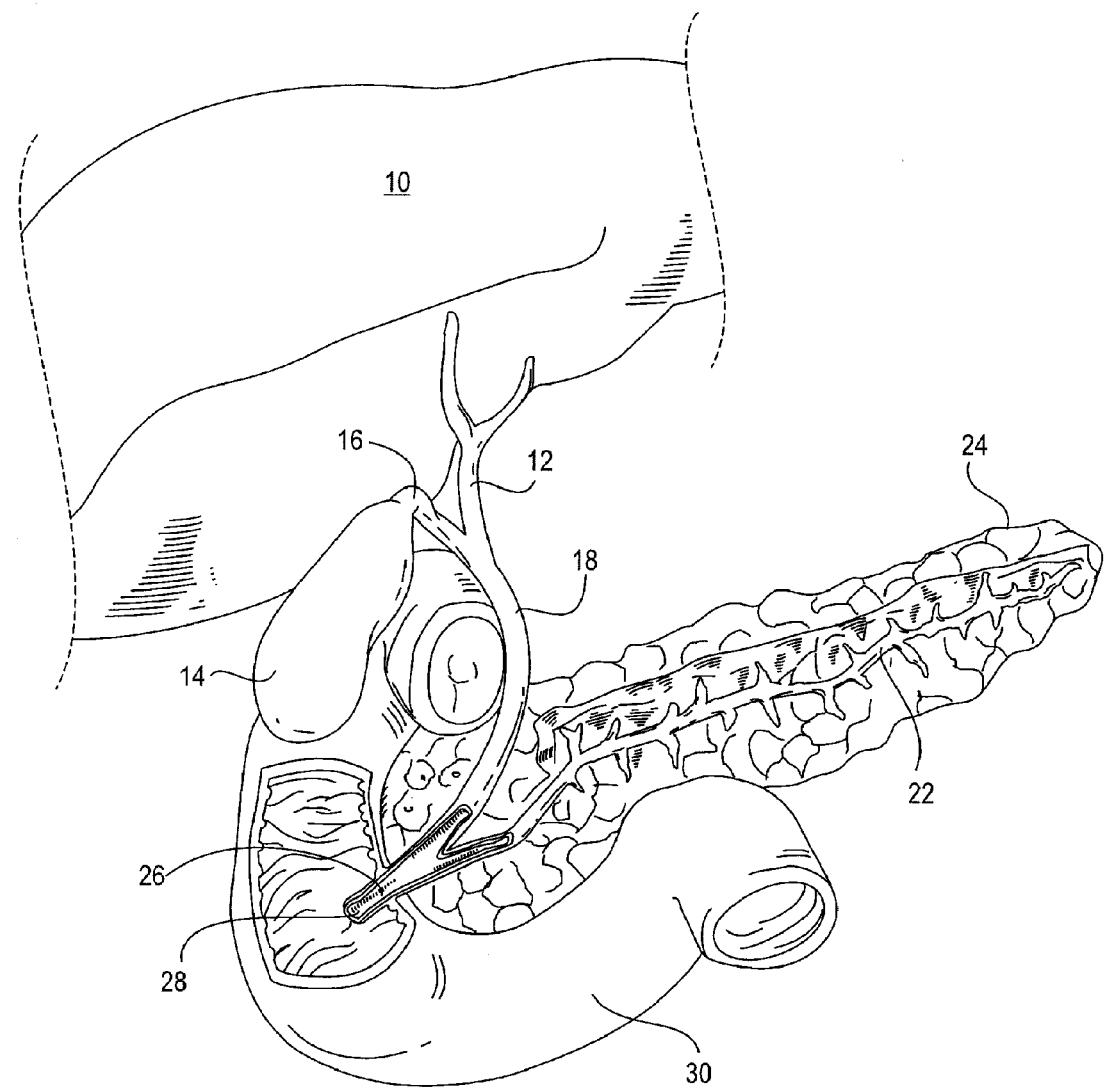
FIG. 1 illustrates an overview of the biliary system.
Figure 2:
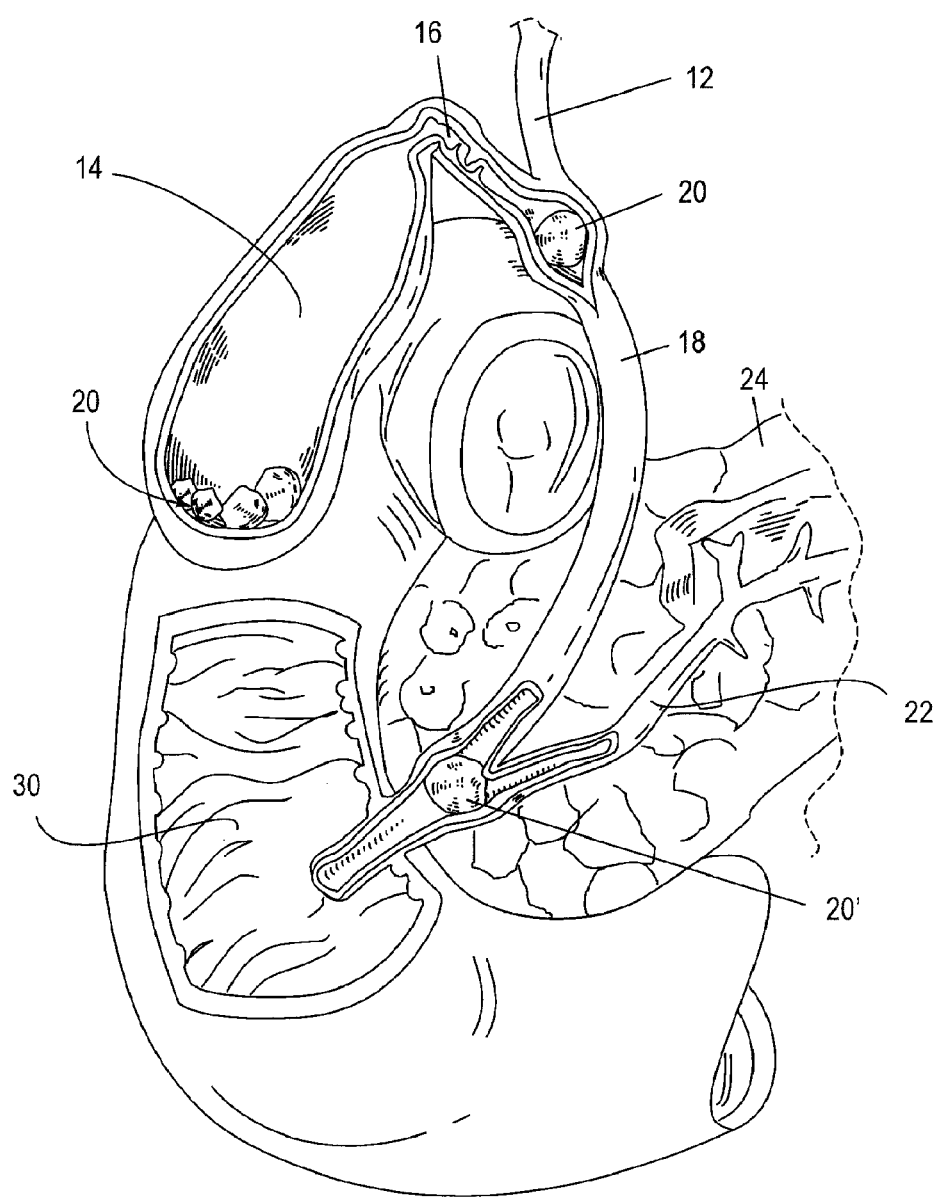
FIG. 2 illustrates the biliary system with gallstones.

For example, they may prove to be an effective mechanism of treating cholangitis (infection of the common bile duct 18). This condition is usually bacterial, and occurs when the bile duct is blocked by gallstones 20 or a tumor. Traditional treatment involves the insertion a stent or drainage catheter into the common bile duct 18 to allow bile to drain into the duodenum from locations above the obstruction. Placement of a conduit into the gallbladder 14 may allow for an alternate method of draining bile and/or other fluids into the duodenum. Any blockage in the common bile duct 18 between the entrance of the cystic duct and the duodenum may be treated in this way. See FIG. 2.

Another use of the devices and techniques described elsewhere in this application may be to create anastomoses between any body lumens in proximity to one another. This may include, but is not limited to: small bowel to small bowel anastomoses, small bowel to large bowel anastomoses, large bowel to large bowel anastomoses, and stomach to small bowel anastomoses. Additionally, creating a conduit between the stomach and other body lumens may be useful and effective for treating and/or managing obesity.

Another use of the devices and techniques described herein is for drainage of any body lumen into another body lumen in proximity, for example, the drainage of pancreatic pseudocysts.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A device for treating biliary disease comprising:
   a component configured for deployment between a gallbladder and a location within a gastrointestinal tract of a patient, the component having a first retaining feature at a proximal end and a second retaining feature at a distal end with a lumen extending therethrough, wherein the component further includes a third retaining feature coupled to the lumen and positioned proximal to the first retaining feature at the proximal end, wherein the third retaining feature is configured to secure tissue of a wall of the gallbladder to the lumen; wherein each of the first retaining feature at the proximal end and the second retaining feature at the distal end are formed into a hemispherical bowl shape that includes one or more fenestrations, and wherein the lumen is formed into a tubular shape in a final configuration; and
   a self-healing plug positioned in the lumen and configured to prevent flow through the lumen, wherein after placement of a hole in the self-healing plug to temporarily allow flow through the lumen, the self-healing plug is configured to self-heal and close the hole to again prevent flow through the lumen.

2. The device of claim 1 wherein a conduit is formed between a gallbladder lumen and a target location within the gastrointestinal tract.

3. The device of claim 2 wherein the target location within the gastrointestinal tract is proximal to a duodenum.

4. The device of claim 1 wherein the device is formed from a bioresorbable material.

5. The device of claim 1 wherein the device is removable.

6. The device of claim 1 wherein the device is expandable.

7. The device of claim 1 further comprising one or more configurations selected from a deployment configuration, a delivery configuration and the final configuration.

8. The device of claim 7 further comprising a variable profile.

9. The device of claim 1 wherein a cross-sectional area of the device is variable along a length.

10. The device of claim 1 wherein the device is configured for deployment by at least one of an endoscope, a needle, a guidewire, a guidance catheter and a dilatation catheter.

11. The device of claim 1 further comprising a flareable end.

12. The device of claim 1 further comprising a configurable retainable feature.

13. The device of claim 1 wherein the component has one or more clips configured to secure the component at one or more positions.

14. The device of claim 1 wherein the lumen is configurable to provide restrictable fluid flow.

15. The device of claim 14 further comprising one or more fluid control components.

16. The device of claim 1 further comprising an enlargeable portion comprising two or more legs.

17. The device of claim 1 further comprising a valve.

18. The device of claim 17 wherein the valve is at least one of a flow-restrictor and a one-way valve.

19. The device of claim 1 wherein the device is flexible.

20. The device of claim 1 wherein the device is an elongate the adapted and configured to extend into the gastrointestinal tract.

21. The device of claim 20 wherein the tube is patent at a first end.

22. The device of claim 21 wherein the patent first end is adjacent the gallbladder.

23. The device of claim 20 wherein the tube is not patent at a second end.

24. The device of claim 20 wherein the tube has an adjustable length.

25. A biliary disease treatment device comprising:
    an implant adapted to be delivered by an endoscope to a gastrointestinal site in proximity to a gallbladder, and further adapted to form a conduit between the gastrointestinal site and the gallbladder;
    wherein each of a first retaining feature at a proximal end of the implant and a second retaining feature at a distal end of the implant are formed into a hemispherical bowl shape that includes one or more fenestrations, and a lumen of the implant is formed into a tubular shape in a final configuration, wherein the implant further comprises a third retaining feature coupled to the lumen and positioned proximal to the first retaining feature at the proximal end, wherein the third retaining feature is configured to secure tissue of a wall of the gallbladder to the lumen; and
    wherein the implant includes a self-healing plug positioned in the lumen and, configured to prevent flow through the lumen, wherein after placement of a hole in the self-healing plug to temporarily allow flow through the lumen, the self-healing plug is configured to self-heal and close the hole to again prevent flow through the lumen.

26. A method for treating biliary disease comprising:
    a. creating a duct or fistula between a gallbladder lumen and a portion of a gastrointestinal tract;
    b. providing for drainage from the gallbladder to the gastrointestinal tract;
    c. delivering a device to the gallbladder through the created duct, the device having a first retaining feature at a proximal end and a second retaining feature at a distal end with a lumen extending therethrough, and wherein the device further includes a third retaining feature coupled to the lumen and positioned proximal to the first retaining feature at the proximal end, wherein the third retaining feature is configured to secure tissue of a wall of the gallbladder to the lumen; wherein each of the first retaining feature at the proximal end and the second retaining feature at the distal end are formed into a hemispherical bowl shape that includes one or more fenestrations and the lumen is formed into a tubular shape in a final configuration; and
    d. placing a self-healing plug in the lumen to prevent flow through the lumen, wherein after placement of a hole in the self-healing plug to temporarily allow flow through the lumen, the self-healing plug is configured to self-heal and close the hole to again prevent flow through the lumen.

27. The method of claim 26 further comprising the step of delivering a substance to the gallbladder via the duct.

28. The method of claim 27 wherein the substances are one or more of antibiotics, inflammatory and anti-inflammatory agents.

29. The method of claim 26 further comprising the step of preventing bile from entering the gallbladder lumen.

30. The method of claim 26 further comprising the step of localizing the gallbladder via endoscopic ultrasound.

31. The method of claim 26 further comprising the step of accessing the gallbladder via the gastrointestinal tract.

32. The method of claim 31 wherein the step of accessing is performed in the gastrointestinal tract at a duodenum.

33. The method of claim 26 further comprising the step of removing Gallstones.

34. The method of claim 26 further comprising the step of altering gallstones.

35. The method of claim 34 further comprising the step of removing the altered gallstones.

36. The method of claim 26 wherein the delivered device is one or more of a stent, a drug-coated stent, and a catheter.

37. The method of claim 26 wherein the biliary disease is treated without removal of the gallbladder.

38. The method of claim 26 further comprising the step of visualizing a treatment area.

39. The method of claim 26 wherein the step of creating the duct further comprises the step of inserting a device in communication between the gastrointestinal tract and the gallbladder lumen.

40. The method of claim 26 wherein the step of creating the duct between a gallbladder lumen and a portion of a gastrointestinal tract comprises the step of inserting a conduit between the gallbladder lumen and the portion of the intestinal tract.

41. The method of claim 40 further comprising the step of forming a biological duct in situ from a patient's tissue.

42. The method of claim 41 wherein the step of inserting a conduit between the gallbladder lumen and the portion of the gallbladder tract occurs at a first time and the step of forming the biological duct in situ from the patient's tissue occurs at a second time remote from the first time.

43. The method of claim 26 further comprising the step of anchoring the device in place.

44. The method of claim 26 further comprising the step of changing the device from a delivery configuration to a deployment configuration.

45. The method of claim 26 further comprising the step of changing the device from a delivery configuration to the final configuration.

46. The method of claim 26 further comprising the step of changing the device from a deployment configuration to the final configuration.

47. The method of claim 26 further comprising the step of reducing a cross-sectional profile of the device.

48. The method of claim 26 further comprising the step of delivering the device via at least one of an endoscope, a needle, a guidewire, a guidance catheter and a dilatation catheter.

49. The method of claim 26 further comprising the step of providing a seal to prevent fluid from leaking into a peritoneum.

50. The method of claim 26 further comprising the step of restricting fluid flow from the gallbladder lumen to the gastrointestinal tract.

51. The method of claim 50 further comprising the step of operating a valve to restrict fluid flow.

* * * * *

UNITED STATES PATENT AND TRADEMARK OFFICE
CERTIFICATE OF CORRECTION

| | |
|---|---|
| PATENT NO. | : 9,486,219 B2 |
| APPLICATION NO. | : 13/439251 |
| DATED | : November 8, 2016 |
| INVENTOR(S) | : Van Dam et al. |

It is certified that error appears in the above-identified patent and that said Letters Patent is hereby corrected as shown below:

In the Specification

In Column 1, Line 5, delete "CROSS-REFERENCE" and insert -- CROSS-REFERENCE TO RELATED APPLICATIONS --, therefor.

In Column 1, Line 7, delete "continuation" and insert -- continuation filed under 35 U.S.C. § 120 --, therefor.

In Column 2, Line 61, delete "cholcystitis" and insert -- cholecystitis --, therefor.

In Column 2, Line 64, delete "ilius" and insert -- ileus --, therefor.

In Column 4, Line 26, delete "cholangiopanctreatograpy" and insert -- cholangiopancreatography --, therefor.

In Column 4, Line 51, delete "cholangiopancreatograpy" and insert -- cholangiopancreatography --, therefor.

In Column 7, Line 23, delete "the or a" and insert -- the --, therefor.

In Column 8, Line 3, delete "illustrates" and insert -- illustrate --, therefor.

In Column 8, Line 6, delete "illustrates" and insert -- illustrate --, therefor.

In Column 8, Line 11, delete "illustrates" and insert -- illustrate --, therefor.

In Column 8, Line 21, delete "illustrates" and insert -- illustrate --, therefor.

In Column 8, Line 21, delete "illustrates" and insert -- illustrate --, therefor.

Signed and Sealed this
Sixth Day of June, 2017

Michelle K. Lee
*Director of the United States Patent and Trademark Office*

CERTIFICATE OF CORRECTION (continued)
U.S. Pat. No. 9,486,219 B2

In Column 8, Lines 43-44, delete "cholagiocarcinoma," and insert -- cholangiocarcinoma --, therefor.

In Column 9, Line 13, delete "laparascopically," and insert -- laparoscopically, --, therefor.

In Column 10, Line 52, delete "hl," and insert -- h1, --, therefor.

In Column 18, Line 10, delete "examplar" and insert -- exemplar --, therefor.

In Column 18, Line 12, delete "examplar" and insert -- exemplar --, therefor.

In the Claims

In Column 21, Line 66, in Claim 20, delete "elongate the" and insert -- elongate tube --, therefor.

In Column 22, Line 26, in Claim 25, delete "and," and insert -- and --, therefor.

In Column 23, Line 4, in Claim 33, delete "Gallstones." and insert -- gallstones. --, therefor.